United States Patent
Johannes et al.

(10) Patent No.: US 11,037,291 B2
(45) Date of Patent: Jun. 15, 2021

(54) SYSTEM AND METHOD FOR DETECTING PLANT DISEASES

(71) Applicant: BASF SE, Ludwigshafen am Rhein (DE)

(72) Inventors: Alexander Johannes, Lambsheim (DE); Till Eggers, Kassel (DE); Artzai Picon, Derio (ES); Aitor Alvarez-Gila, Derio (ES); Amaya Maria Ortiz Barredo, Vitoria-Gasteiz (ES); Ana Maria Diez-Navajas, Vitoria-Gasteiz (ES)

(73) Assignee: BASF SE, Ludwigshafen (DE)

( * ) Notice: Subject to any disclaimer, the term of this patent is extended or adjusted under 35 U.S.C. 154(b) by 212 days.

(21) Appl. No.: 16/300,988

(22) PCT Filed: Apr. 19, 2017

(86) PCT No.: PCT/EP2017/059231
§ 371 (c)(1),
(2) Date: Nov. 13, 2018

(87) PCT Pub. No.: WO2017/194276
PCT Pub. Date: Nov. 16, 2017

(65) Prior Publication Data
US 2020/0320682 A1 Oct. 8, 2020

(30) Foreign Application Priority Data
May 13, 2016 (EP) ..................................... 16169719

(51) Int. Cl.
*G06K 9/00* (2006.01)
*G06T 7/00* (2017.01)
(Continued)

(52) U.S. Cl.
CPC ........... *G06T 7/0012* (2013.01); *G01N 21/27* (2013.01); *G01N 33/0098* (2013.01);
(Continued)

(58) Field of Classification Search
CPC ..................... G06T 7/0012; G06T 7/90; G06T 2207/20076; G06T 2207/20081;
(Continued)

(56) References Cited

U.S. PATENT DOCUMENTS

| | | | |
|---|---|---|---|
| 7,911,517 B1 * | 3/2011 | Hunt, Jr. .............. | G06K 9/0063 348/272 |
| 10,719,936 B2 * | 7/2020 | Paschalakis ......... | G06K 9/6257 |
| 2014/0036054 A1 * | 2/2014 | Zouridakis ........... | A61B 5/0077 348/77 |

OTHER PUBLICATIONS

Johannes, Alexander, et al. "Automatic plant disease diagnosis using mobile capture devices, applied on a wheat use case." Computers and electronics in agriculture 138 (2017): 200-209. (Year: 2017).*

(Continued)

*Primary Examiner* — Jonathan S Lee
(74) *Attorney, Agent, or Firm* — Marshall, Gerstein & Borun LLP

(57) ABSTRACT

A system (100), method and computer program product for determining plant diseases. The system includes an interface module (110) configured to receive an image (10) of a plant, the image (10) including a visual representation (11) of at least one plant element (1). A color normalization module (120) is configured to apply a color constancy method to the received image (10) to generate a color-normalized image. An extractor module (130) is configured to extract one or more image portions (11e) from the color-normalized image wherein the extracted image portions (11e) correspond to the at least one plant element (1). A filtering module (140) configured: to identify one or more clusters (C1 to Cn) by
(Continued)

one or more visual features within the extracted image portions (11e) wherein each cluster is associated with a plant element portion showing characteristics of a plant disease; and to filter one or more candidate regions from the identified one or more clusters (C1 to Cn) according to a predefined threshold, by using a Bayes classifier that models visual feature statistics which are always present on a diseased plant image. A plant disease diagnosis module (150) configured to extract, by using a statistical inference method, from each candidate region (C4, C5, C6, Cn) one or more visual features to determine for each candidate region one or more probabilities indicating a particular disease; and to compute a confidence score (CS1) for the particular disease by evaluating all determined probabilities of the candidate regions (C4, C5, C6, Cn).

13 Claims, 11 Drawing Sheets

(51) Int. Cl.
　　　*G06T 7/90*　　　(2017.01)
　　　*G01N 21/27*　　(2006.01)
　　　*G01N 33/00*　　(2006.01)
　　　*G06K 9/46*　　　(2006.01)
　　　*G06K 9/62*　　　(2006.01)
　　　*G06N 3/04*　　　(2006.01)
　　　*G06N 3/08*　　　(2006.01)

(52) U.S. Cl.
　　　CPC ......... *G06K 9/4647* (2013.01); *G06K 9/4652* (2013.01); *G06K 9/6221* (2013.01); *G06K 9/6278* (2013.01); *G06N 3/04* (2013.01); *G06N 3/08* (2013.01); *G06T 7/90* (2017.01); *G06T 2207/20076* (2013.01); *G06T 2207/20081* (2013.01); *G06T 2207/20084* (2013.01); *G06T 2207/30188* (2013.01)

(58) Field of Classification Search
　　　CPC ........... G06T 2207/20084; G06T 2207/30188; G01N 21/27; G01N 33/0098; G06K 9/4647; G06K 9/4652; G06K 9/6221; G06K 9/6278; G06N 3/04; G06N 3/08
　　　USPC ......................................................... 382/110
　　　See application file for complete search history.

(56) References Cited

OTHER PUBLICATIONS

Prasad, Shitala, Sateesh K. Peddoju, and Debashis Ghosh. "Multi-resolution mobile vision system for plant leaf disease diagnosis." Signal, Image and Video Processing 10.2 (2016): 379-388. (Year: 2016).*

Siricharoen, Punnarai, et al. "A lightweight mobile system for crop disease diagnosis." International conference on image analysis and recognition. Springer, Cham, 2016. (Year: 2016).*

Wang, Guan, Yu Sun, and Jianxin Wang. "Automatic image-based plant disease severity estimation using deep learning." Computational intelligence and neuroscience 2017 (2017). (Year: 2017).*

Ubbens, Jordan R., and Ian Stavness. "Deep plant phenomics: a deep learning platform for complex plant phenotyping tasks." Frontiers in plant science 8 (2017): 1190. (Year: 2017).*

Hu, Gensheng, et al. "A low shot learning method for tea leaf's disease identification." Computers and Electronics in Agriculture 163 (2019): 104852. (Year: 2019).*

Aravind, K. R., et al. "Grape crop disease classification using transfer learning approach." International Conference on ISMAC in Computational Vision and Bio-Engineering. Springer, Cham, 2018. (Year: 2018).*

Ramesh, Shima, et al. "Plant disease detection using machine learning." 2018 International conference on design innovations for 3Cs compute communicate control (ICDI3C). IEEE, 2018. (Year: 2018).*

Alexander Johannes, et al., "Automatic plant disease diagnosis using mobile capture devices, applied on a wheat use case", Computers and Electronics in Agriculture, Elsevier, Amsterdam, NL, vol. 138, May 8, 2017, pp. 200-209, XP085024313.

Miaienborn, Claudia et al., "Semantics an International Handbook of Natural Language Meaning" In: "Semantics an International Handbook of Natural Language Meaning", Jan. 1, 2011, De Gruyter Mouton, XP055357650, p. 1485.

Sankaran, S., et al. "A review of advanced techniques for detecting plant diseases", Computers and Electronics in Agriculture, Elsevier, Amsterdam, NL, vol. 72, No. 1, Jun. 1, 2010, pp. 1-13, XP026995685, ISSN: 0168-1699 [retrieved on Apr. 9, 2010].

Sannakki Sanjeev S., et al. "Leaf Disease Grading by Machine Vision and Fuzzy Logic", International Journal of Computer Technology and Applications, Sep. 1, 2011, pp. 1709-1716, XP055385562, Retrieved from the Internet: URL:http://www.ijcta.com/documents/volumes/vol2issue5/ijcta2011020576.pdf.

Mohanty, Sharada P., et al. "Using Deep Learning for Image-Based Plant Disease Detection", Frontiers in Plant Science, Sep. 22, 2016, pp. 1-10, XP055385570, DOI:10.3389/fpls.2016.01419 Retrieved from the Internet: URL:https://www.ncbi.nlm.nih.gov/pmc/articles/PMC5032846/pdf/fpls-07-01419.pdf.

Sladojevic, Srdjan, et al., "Deep Neural Networks Based Recognition of Plant Diseases by Leaf Image Classification", Computational Intelligence and Neuroscience, May 29, 2016, pp. 1-11, XP055385550, Retrieved from the Internet: URL:http://downloads.hindawi.com/journals/cin/2016/3289801.pdf.

Xie, Xinhua,et al. "A system for diagnosis of wheat leaf diseases based on Android smartphone", SPIE—International Society for Optical Engineering. Proceedings, Spie International Society for Optical Engineering, US, vol. 10155, Oct. 19, 2016, pp. 1015526-1015526, XP060078810, Issn:.

Zhou Jun et al., "Computer Vision and Pattern Recognition in Environmental Informatics", Jan. 1, 2015, IGI Global, XP055309262, pp. 296-322.

International Search Report dated Jul. 5, 2017, prepared in International Application No. PCT/EP2017/059231.

International Preliminary Report on Patentability dated Jul. 5, 2018, prepared in International Application No. PCT/EP2017/059231.

* cited by examiner

SYSTEM AND METHOD FOR DETECTING PLANT DISEASES

This application is a National Stage application of International Application No. PCT/EP2017/059231, filed Apr. 19, 2017. This application also claims priority under 35 U.S.C. § 119 to European Patent Application No. 16169719.8, filed May 13, 2016.

TECHNICAL FIELD

The present invention generally relates to the determination of plant diseases and more particularly to image based diagnostics for plant diseases with statistical inference method support.

BACKGROUND

Some plant diseases show disease specific indicators on the surface of the plant leafs. For example, fungal diseases such as Fungal early diseases (e.g., Septoria, *S. tritici* and *S. nodorum*), Fungal late diseases (e.g., Wheat Rusts), and *Helminthosporium* typically cause a change of the plant leafs in that they show disease specific spots or blobs which can be visually analyzed.

Computerized visual diagnostic methods have been proposed in the past. For example, the paper "Leaf Disease Grading by Machine Vision and Fuzzy Logic" (by Arun Kumar R et al, Int. J. Comp. Tech. Appl., Vol 2 (5), 1709-1716) discloses an approach to automatically grade diseases on plant leaves. The proposed system uses image processing techniques to analyze color specific information in an image of the diseased plant. A K-means clustering method is performed for every pixel in the image to extract clusters with diseased spots. The segmented image is saved and the total leaf area is calculated. Finally, the disease spreading on plant leaves is graded by employing Fuzzy Logic to determine a particular disease. A high computational effort is required for such an image processing based method.

In "Computer Vision and Pattern Recognition in Environmental Informatics", Jun Zhou et al, IGI Global, 2015, Chapter 14 "Cell Phone Image-Based Plant Disease Classification" a computational framework for plant disease diagnostics is presented. Various image descriptors are proposed, such as color channels, image gradients, LBP, etc. together with erosion algorithms which extract the desired features. In a preprocessing stage a color filter is used and a threshold value is set. Values higher than this threshold form a binary image of a candidate region which is filtered using morphology. A subsequent feature extraction is performed by calculating the features for each connected region extracted from the previous step or by the whole image. However, the disclosed solution does not propose how to determine a global presence of a particular disease. Instead, several candidates are detected and analyzed separately which may be less reliable. Further, the disclosed disease analysis is less robust against light conditions when recording a plant image of a diseased plant because it does not allow for illumination and/or photography changes on the recorded image and adapt to them.

SUMMARY

There is a need to provide image processing based plant disease identification while reducing the computational efforts required by prior art systems and, at the same time, improve the reliability of the disease identification.

Embodiments of the invention as disclosed in the independent claims provide system, method and computer program product to detect plant diseases by image processing based techniques in combination with a statistical inference method to solve the above technical problem. Plant disease detection as used herein includes the determination of a probability that a particular disease is present. Typically, plant diseases cause characteristic damage on the surface of plant elements (e.g., leaf, root, blossom, fruit, flower, stem, etc.). Therefore, characteristic spots or blobs become visible on some elements of a diseased plant.

In one embodiment, a system for detecting plant diseases includes an interface module configured to receive an image of a plant. For example, the image may be recorded by a digital camera which is communicatively coupled with the system. The system can be a computing system, such as for example, a Personal Computer, a server computer, a smartphone, a tablet computer, etc. For example, the camera may be connected with the system via a Universal Serial Bus (USB) interface or it may communicate with the system via a wireless communication standard (e.g., Bluetooth). The camera may be a web cam or any other digital camera including professional high resolution cameras. In some embodiments, the camera may an integral part of the system as it is typically the case with smartphones or tablet computers in which case the interface module is a system internal interface. The image recorded by the camera includes a visual representation of at least one plant element. In the following description, a plant leaf is used as a representative of a plant element. However, a person skilled in the art can apply the teaching in the context of a plant to any other element of the plant. The at least one plant leaf belongs to a plant (e.g., crop, wheat, etc.) and is subject to further analysis regarding potential diseases. The image may be stored by the system in a memory portion of the system where it can be accessed by various image processing modules of the system.

The system further has a color normalization module which applies a color constancy method to the received image to generate a color-normalized image. The color normalization module can be implemented by image processing functions to perform the color constancy method by processing the pixels of the received image accordingly. For example, suitable color constancy methods are: Shades of gray algorithm (cf. G. D. Finlayson and E. Trezzi, "Shades of Gray and Colour Constancy", Color and Imaging Conference, vol. 2004, no. 1, pp. 37-41, January 2004.), Gray world algorithm (cf. G. Buchsbaum, "A spatial processor model for object colour perception," Journal of the Franklin institute, vol. 310, no. 1, pp. 1-26, 1980), Gray edge algorithm (cf. J. van de Weijer, T. Gevers, and A. Gijsenij, "Edge-Based Color Constancy," IEEE Transactions on Image Processing, vol. 16, no. 9, pp. 2207-2214, September 2007), and Max-RGB algorithm (cf. E. H. Land and J. J. McCann, "Lightness and retinex theory," JOSA, vol. 61, no. 1, pp. 1-11, 1971; E. H. Land, "The retinex theory of color vision," Scientific American, vol. 237, no. 6, p. 108, 1977). Color normalization methods may be used to reduce or even eliminate effects which are caused by different illumination situations. For example, a first image may be recorded with the sun shining, a second image may be recorded on a rainy day. For the further processing of such images it is advantageous to have color-normalized images as starting point for the disease analysis which very similar in the sense that there is only a low color variability due different illumination situations.

The system further has an extractor module configured to extract one or more image portions from the color-normalized image. The plant element extraction (e.g., leaf segmentation) is facilitated when being performed on a color-normalized image instead of the originally recorded image. Plant element extraction is set up in such a way that the extracted portions extracted from the color-normalized image correspond (relate) to the at least one plant element. That is, the extractor performs image processing operations which segment the portions of the image associated with plant elements from other portions in the image (e.g., image background). Different embodiments of the extractor are possible. For example, a leaf extractor may use a Gray-plate Segmentation algorithm as extraction method. The Gray-plate Segmentation uses color saturation and border information to extract the image portions which correspond to the at least one plant element. Alternatively, a Manual Segmentation algorithm may be used as extraction method. Thereby, a plant element mask is received by the system as input from a user and Chan-Vese segmentation may be used to smooth and refine the received mask. In another embodiment, a Natural Image Segmentation algorithm may be used as extraction method. Natural Image Segmentation uses pre-segmentation of the color-normalized image by means of color distributions and analyzes each blob of the image with border distribution, color and LBP-based texture to measure its probability of belonging to a plant element.

In one optional embodiment, the color normalization module is further configured to apply one or more color constancy methods to the extracted one or more image portions to color-normalize the extracted one or more image portions. Such an additional color-normalization step applied to the extracted portions can further improve the image for the following image processing stages of the system and facilitate object identification in the image.

The system further has a filtering module. The filtering module can perform two functions which result in a reliable identification of portions of the image which include such portions of the plant element(s) that show plant disease characteristics. The first function of the filter is a clustering function configured to identify clusters by one or more visual features within the extracted image portions. Each identified cluster is associated with a portion of a plant element showing characteristics of a plant disease. Advantageously, the visual features can be color channels such as, for example, R,G,B,H,S,L,a,b and/or other color channels to emphasize diseases. Other visual clustering features (e.g., texture), may be used instead of or in addition to color channels. The second function is a naive Bayes classifier (also simply referred to as Bayes classifier herein) that models visual feature statistics which are always present on images showing plants with respective diseases. The Bayes classifier acts as a filter to filter the identified clusters according to a predefined threshold. The predefined threshold is configured to determine one or more candidate regions and controls the percentage of detected element portions to qualify as candidate regions showing characteristics of a plant disease. For example, the threshold may be set in a training procedure when training the Bayes classifier via a training module. The filter function applied by the Bayes classifier has a high degree of reliability in identifying true positives as candidate regions for the further image processing. For example, the threshold can be set in such a way that 99% of the filtered element portions actually show characteristics of one or more diseases. In view of the full image content the identified candidate regions typically cover only a relatively small number of pixels when compared to the number of pixels of the entire image. As a consequence, the amount of data which is used as the basis for the next stages of image processing is significantly reduced by the Bayes filter mechanism which significantly reduces the data processing effort of the following image processing stages.

In one optional embodiment, different plant diseases may be associated with different image-disease-characteristics and the filtering module may be further configured to cluster the extracted image portions by plant disease in accordance with identified image-disease-characteristics. For example, different diseases may be associated with different color channels and the clustering step can already perform the clustering by color channel (i.e., by disease). Thereby, the Bayes classifier can also be based on multiple color channels. For example, the filtering can be performed over selected color channels including Lab, HSL, and specific color channels to map properties in septoria disease. For example, the segmented region may be refined by means of morphologic operations such as dilating and eroding. Special processing can be tuned up to detect the inner and outer regions of septoria-like diseases.

In case no candidate regions are determined by the filtering module when using the predefined restrictive threshold, the filtering module checks again with a less restrictive threshold on a second attempt of detection. In other words, the filtering module may perform multiple iterations of the previously described filtering mechanism and, in each iteration, the predefined threshold may be modified (e.g., decreased) until at least one candidate region is identified.

In case no candidate regions at all are determined by the filtering module when using the predefined threshold(s), the filtering module determines the cluster with the highest probability as candidate region for the following image processing stages.

The system further includes a plant disease diagnosis module which finally determines which disease is present on the photographed plant. The diagnosis module also performs two functions.

In a first function, a base classifier extracts from each candidate region one or more visual features to determine for each candidate region one or more probabilities indicating a particular disease. The base classifier uses a statistical inference method for determining the probabilities. In one embodiment, the base classifier extracts visual descriptors and classifiers from the candidate regions and uses machine learning techniques to determine the one or more probabilities. In another embodiment, the statistical inference method performs visual feature extraction from the candidate regions by means of a convolutional neural network architecture and uses deep learning techniques to determine the one or more probabilities.

In a second function of the plant disease diagnosis module, a meta-classifier computes a confidence score for the particular disease by evaluating all determined probabilities of the candidate regions.

The proposed system can provide reliable diagnostic results for plant diseases via image processing techniques applied to an image of a diseased plant. The system is efficient in that it does not process the entire image in all stages of the disease determination method but applies a Bayes filter on a color-normalized version of the image which significantly reduces the amount of data to be processed. This allows to use less powerful hardware or to free up computing resources of the system (memory and CPU power) for other tasks.

Further aspects of the invention will be realized and attained by means of the elements and combinations particularly depicted in the appended claims. It is to be understood that both the foregoing general description and the following detailed description are exemplary and explanatory only, and are not restrictive of the invention as described.

DETAILED DESCRIPTION

Figure 1:
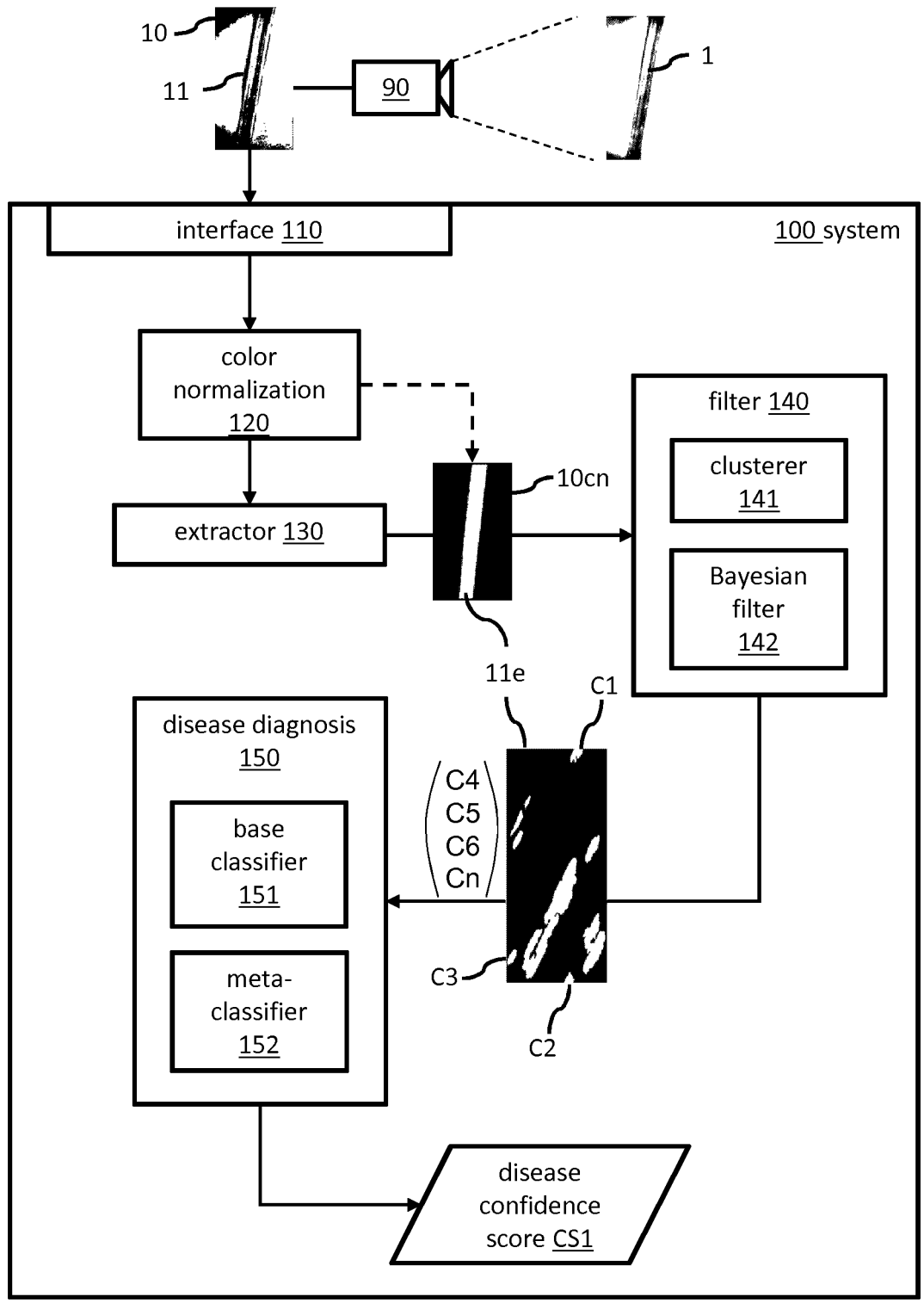
FIG. 1 is a simplified block diagram of a system for detecting plant diseases according to an embodiment of the invention.
Figure 2:
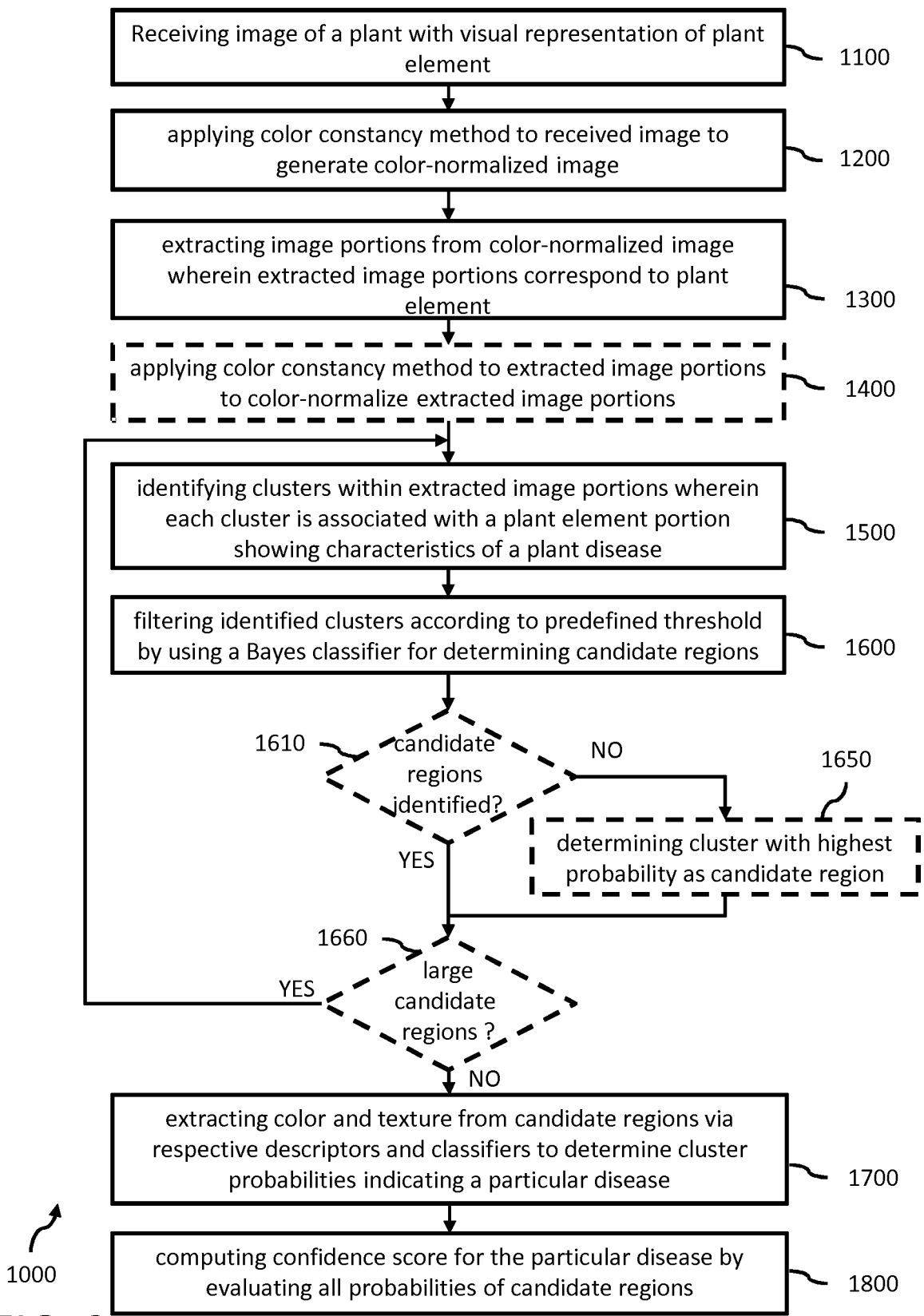
FIG. 2 is a simplified flow chart of a method for detecting plant diseases performed by the system according to an embodiment of the invention.

FIG. 1 is a simplified block diagram of a system 100 for detecting plant diseases according to an embodiment of the invention. FIG. 1 will be discussed in the context of FIG. 2 which is a simplified flow chart of a method 1000 for detecting plant diseases performed by the system 100 of FIG. 1 according to an embodiment of the invention. Reference numbers therefore may refer to FIG. 1 or FIG. 2.

The system 100 may be any computing device which is equipped with appropriate hardware and software to perform the image processing steps and statistics disclosed in the following description. The system may be a general purpose computer but it can also be a mobile device such as a smartphone or tablet computer with adequate computation resources (memory, CPU, software modules). For example, the system 100 may be a handheld device carried by a farmer who is inspecting a field with crop plants and who wants to analyze plant samples showing conspicuous features which may indicate a plant disease (e.g., fungal early diseases such as Septoria, *S. tritici* and *S. nodorum*; fungal late diseases such as Wheat Rusts, or *Helminthosporium*.)

In one embodiment, the handheld device (e.g., smartphone) may include a digital camera 90 which can be used by the farmer to record an image 10 of a suspect plant. The image 10 includes a visual representation 11 of at least one plant element 1. In the example the plant element is a leaf 1.

In some embodiments, the system 100 may be a remote server or a computer which is installed on the farmer's tractor and the farmer may use a handheld device with the camera 90 to take the picture of the plant wherein picture can be communicated from the camera to the remote system 100 via an appropriate interface. Mobile communication standards may be used to establish the communicative coupling of the camera 110 with the system 100.

In one embodiment, a selected mobile device (e.g. smartphone) may be equipped with specific microscopy lenses and an illumination system, or it may be communicatively coupled with a handheld digital microscope (e.g., ProScope HR offered by Bodelin Technologies, Wilsonville, USA) via an USB interface to provide high magnification images of plant leafs.

The recorded image 10 is received 1100 by the system 100 via the interface 110. In such embodiments where the camera 90 is an integrated component of the system 100 the interface 110 may just be an internal bus which is configured to exchange image data between different components or modules of the system 100. The received image data 10 is stored or buffered in a corresponding portion of the memory (not shown) of system 100. For example, the memory may have a particular portion which is reserved for storing image data in respective formats (e.g., JPEG, PDF, PNG, etc.). Image processing functions as disclosed herein can then access and process the image at its respective storage/buffer location.

The system 100 includes the color normalization module 120 (CNM). The CNM 120 can apply 1200 a color constancy method to the entire received image 10 to generate a color-normalized image. Typically, the recorded image 10 may present a color variability that can be reduced by using color constancy methods such as, for example, Shades of gray algorithm, Gray world algorithm, Gray edge algorithm, or Max-RGB algorithm. A color constancy method uses external information such as, for example, neutral chromatic information of a reference object of a known color (e.g., a gray plate or gray card). This information can be used to model the lighting conditions which were present while the image was recorded, and to perform external reference-based color normalization that maps the taken (recorded) colors to a common color reference system. Color normalization makes the corrected images more robust to changing illumination conditions during the recording of the images.

Results can be further improved by analyzing and developing color normalization models for the recorded images. Models can be trained with different camera devices and inter-device tests can be performed. The color contrast may vary between different camera types. For example, if a given camera device takes pictures with very pale colors and another camera device takes very colorful pictures, a training which is only based on the images of the device exhibiting colorful images may lead to missing a disease characterized by colorful spots the image was recorded by the pale color camera device. In this example, the appearance of the respective spots would not be as colorful as expected by the respective classifier trained with the camera device that captures the more colorful pictures. The applied color constancy method removes or at least weakens differences related to the acquisition parameters and hardware parameter of the various camera devices. This leads to better classification results. Retrained models based on images acquired using a gray plate as background obtain better results than images showing a natural background. Therefore, a gray-plate may be suitable for improving the system accuracy with regards to disease identification.

Nevertheless, it may be interesting to support several camera devices with the same models. This may be achieved, for example, by training the models with images of several devices. Alternatively, or in addition, each camera device may be parameterized to automatically normalize color mapping, resolution and magnification. Alternatively, or in addition, image normalization methods can be developed to reduce the variability in the image acquisition/recording conditions.

The extractor module 130 (EM) of the system 100 can then extract 1300 one or more image portions 11e from the color-normalized image wherein the extracted image portions 11e correspond to the at least one plant element 1 (e.g., leaf, root, blossom, fruit, flower, stem, etc.). That is, the EM 130 can reduce the image content to the relevant portions of the image where graphical representations of leafs are shown. The image background cannot provide any meaningful information for the disease identification of the plants. For the leaf extraction various methods may be used by the EM 130. For example, a Gray-plate Leaf Segmentation algorithm may be used which uses color saturation and border information to extract the image portions 11e correspond to the at least one plant leaf 1. In another example, a Manual Leaf Segmentation algorithm may be used where a leaf mask is received as input from a user and, subsequently, Chan-Vese segmentation is used to smooth and refine the received mask. In another example, a Natural Image Segmentation algorithm is used which uses pre-segmentation of the color-normalized image by means of color distributions and which analyzes each blob with border distribution, color and LBP-based texture to measure its probability of belonging to a leaf of the plant. The three embodiments of the EM 130 are discussed in more detail in the context of FIGS. 7A to 7C.

As a result of the plant element extraction (e.g., leaf segmentation), only such portions of the color-normalized image 10cn belonging to the graphical representation 11 of the leaf in the original image are identified by the leaf segmentation algorithms. Thereby, not necessarily all of such portions need to be identified.

In an optional embodiment of system 100, CNM 120 may be further configured to apply 1400 one or more color constancy methods to the extracted one or more image portions 11e provided by the EM 130 to further color-normalize the extracted one or more image portions. By re-applying color constancy methods to the extracted element portions of the image an improved color-normalized image 10cn can be generated because the color constancy methods are only applied to potentially relevant parts of the image, thus, avoiding artificial color normalization effects which may be caused by irrelevant background portions (e.g., soil, stones, etc.) included in the full image.

The system 100 further has a filtering module 140 (FM). The FM 140 is used for a primary segmentation of the extracted portions of plant elements of the image by performing a clustering for such element portions. Further, the FM 140 performs a Bayesian check on the identified clusters to mask and pre-select regions on the plant element which show characteristics of a plant disease. Such pre-selected regions are then presented as candidate regions to further analysis modules of the system 100.

The primary segmentation can be performed by a clustering sub-module 141. Segmentation by clustering is well known in the art (cf. "Computer Vision—A Modern Approach", by Forsyth, Ponce, Pearson Education ISBN 0-13-085198-1, pages 301 to 3017). The clusterer 141 may also be implemented as an independent module in the system 100 which receives the extracted plant element portions 11e from the EM 130. The clusterer 141 identifies 1500 one or more clusters C1 to Cn by one or more visual features within the extracted image portions 11e. A cluster is a group of pixels having similar visual feature values (e.g., color values or textural values). Thereby, each cluster is associated with a leaf portion showing characteristics of a plant disease. For example, clustering of the extracted portions 11e may be based on a single color channel (e.g., dark levels of the b channel). However, the increased complexity and variability of new diseases can be better handled by the clusterer 141 when supporting a multi-color channel approach. With a multi-color channel approach the FM 140 becomes tunable for new diseases. That is, flexibility of the FM 140 is improved. For example, different colors may represent different diseases. In this embodiment, clustering the extracted image portions may result in clusters sorted by plant disease in accordance with identified image-disease-characteristics wherein a particular disease is associated with a particular color. A list of segmentation parameters which may be used to identify characteristics of a plant disease for clustering includes, among others, the visual features such as one or more color channels or textural features. Also configuration features like the number of clusters, the selected recall percentage for the diseased clusters, the color channel or visual features included, the necessity of a hierarchical clustering or the reduction of the leaf area can be used as segmentation parameters.

The one or more visual features for clustering can be color descriptors or texture descriptors selected from the group of:
Local L,a,b,H,S,R,G or B color channel mean and variance;
Local L,a,b,H,S,R,G or B color channel color histogram;
"Local Opponent Color mapping" histogram;
Local Binary Pattern (LBP) descriptor over L,a,b,H,S,R,G or B channels;
Uniform LBP descriptor over L,a,b,H,S,R,G or B channels;
Uniform LBP descriptor over LOC mapping;
DSIFT like descriptor over L,a,b,H,S,R,G or B channels;
Advanced color filter bank LINC and SLINC; and
any of the previous descriptors quantified and encoded in visual words.

Figure 3:
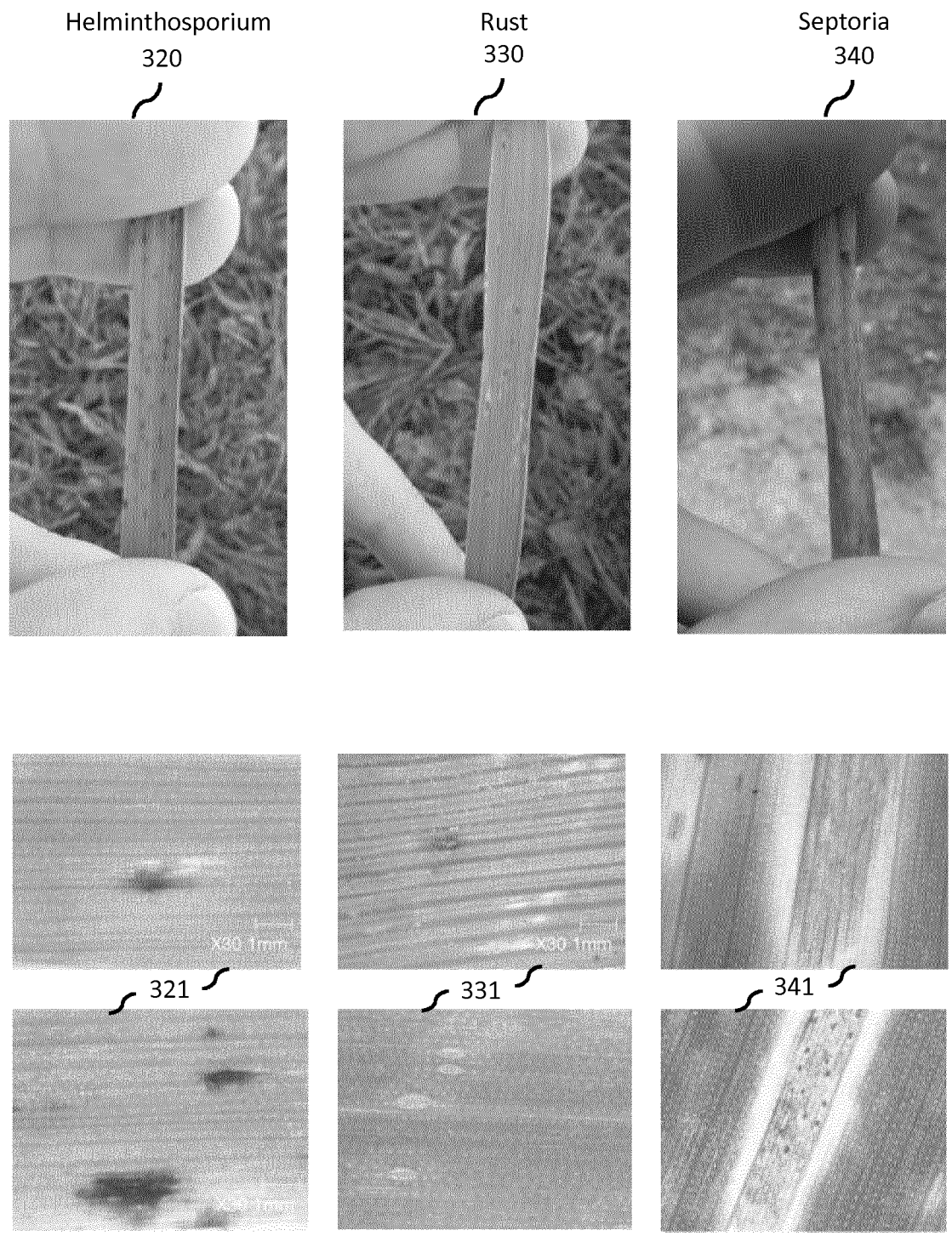
FIG. 3 shows photographs of plant leafs with three different plant diseases.

For example, the diseases rust and *Helminthosporium* are totally visually different. This can be seen in the images of FIG. 3. Image 320 shows *Helminthosporium* on a leaf recorded with a low magnification camera of a smartphone. The images 321 are recorded with a magnification device and show the same disease. Image 330 shows rust on a leaf recorded with a low magnification camera. The images 331 are recorded with a magnification device and show the same disease. Nevertheless, rust and *Helminthosporium* share a significant amount of similarities as they cause relatively small localized spots on the leaf surface. However, septoria (cf. FIG. 3, low magnification image 340, high magnification images 341) is a totally different kind of disease that typically affects the overall visual appearance of the leaf as it affects larger regions of the leaf surface. Therefore, a particular configuration for the FM 140 can be generated to also include the visual features of the septoria disease in the clustering. For example, large area disease blobs (e.g., septoria) typically show outer and inner rings as a characteristic feature. The primary segmentation module can support the detection of such visual features by including such characteristics in the respective model used by the clusterer 141.

Figure 4A:
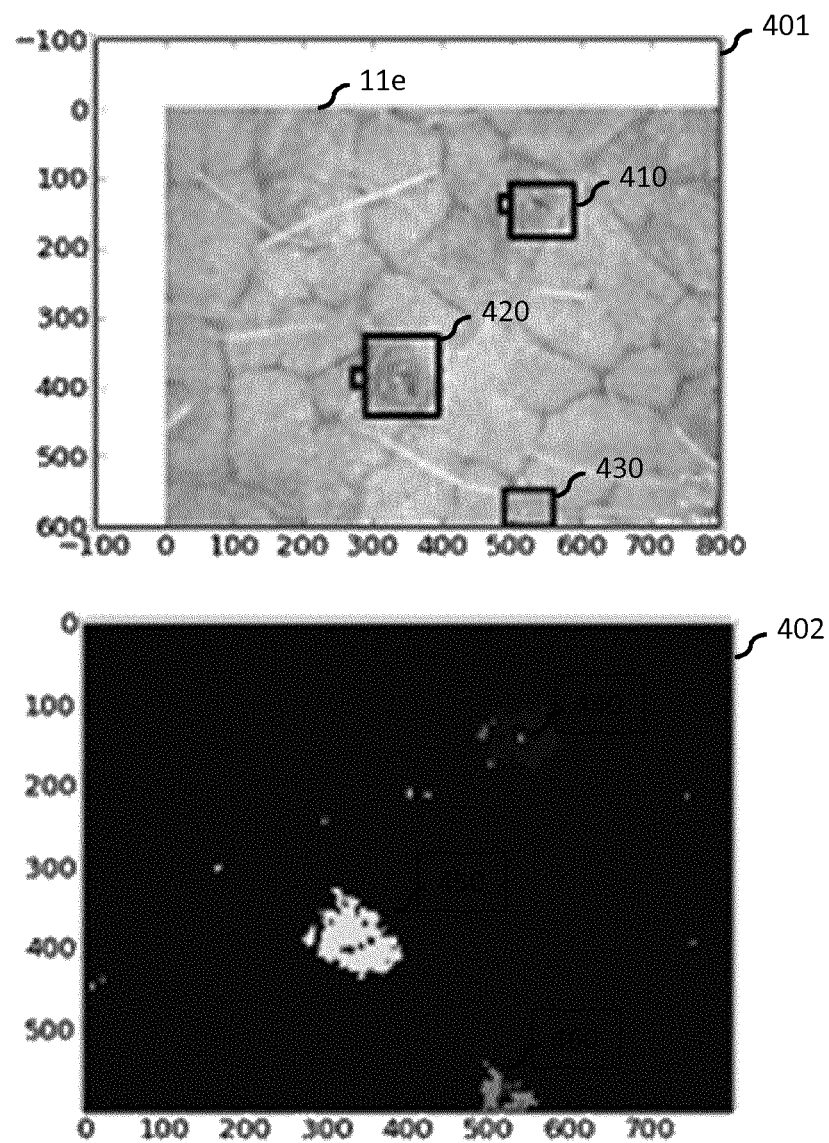
FIG. 4A, 4B show examples of clustering results according to embodiments of the invention.
Figure 4B:
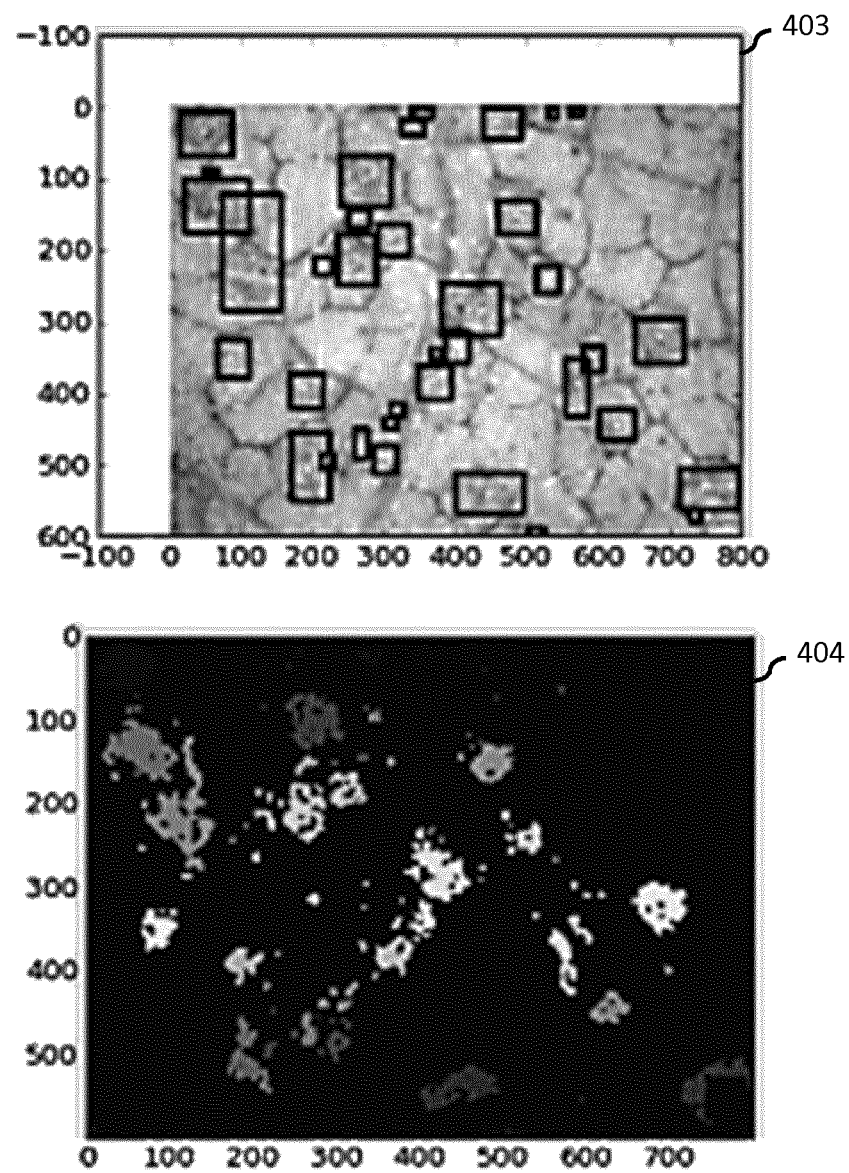

FIGS. 4A, 4B show examples of clustering results of the clusterer 141 where the color-normalized extracted leaf portions are clustered by respectively configured color channel(s). The horizontal and vertical scales relate to the pixel coordinates of the image 11e. In the upper part 401 of FIG.

4A three color clusters 410, 420, 430 are identified which are clustered according to their color channels in a multi-color channel embodiment as can be seen in the corresponding lower part 402. In the example, each identified cluster has a different color for computational identification. The respective spots 440, 450, 460 associated with those color clusters 410, 420, 430 are shown in the lower part 402. Each spot corresponds to an object which is defined by the visual feature values (e.g. colors) of the respective cluster. In the examples, each spot is drawn in a different color to allow computational differentiation among each spot. Thereby, a range of colors may be mapped to the same disease detectable by the Bayesian check. FIG. 4B shows another example of a leaf portion with a higher density of color clusters (indicated by the black rectangles in the upper part 403) and corresponding spots in the lower part 404.

Back to FIG. 1, a second function of filter 140 includes a Bayesian filter function 142 which performs a Bayesian check on the identified clusters. Thereby, a Bayes classifier is used to filter 1600 the identified one or more clusters C1 to Cn according to a predefined threshold. The Bayes classifier models visual feature statistics which are always present on a diseased plant image like the visual characteristics shown on FIG. 3 (showing diseased plant images of three plants with each plant having a particular respective disease). Examples of visual feature statistics include an image color statistics taken from one selected color channel or a combination of color channels selected from the following list: Lab, Mean_ab, RGB, HSI, Norm rgb, CMYK and XYZ. Such color channels are known by a person skilled in the art.

The visual feature statistics of each identified cluster is then confronted with this Bayesian segmentation model. Each identified image cluster is analyzed and its disease likelihood probability is calculated and is segmented by using the Bayes segmentation model which is biased according to the predefined threshold to ensure a low percentage (e.g., between 1% and 5%) of discarded positives while maintaining a low rate of false positives. That is, after the application of the Bayesian filter 142 to the clusters C1 to Cn (which are identified by the clusterer 141) only such clusters which pass the Bayesian check with the predefined threshold are kept as candidate regions (e.g., C4, C5, C6, Cn— illustrated as a vector in FIG. 1) for further analysis. In other words, the predefined threshold ensures that every candidate region in the image will be segmented for further deeper analysis.

Figure 5:
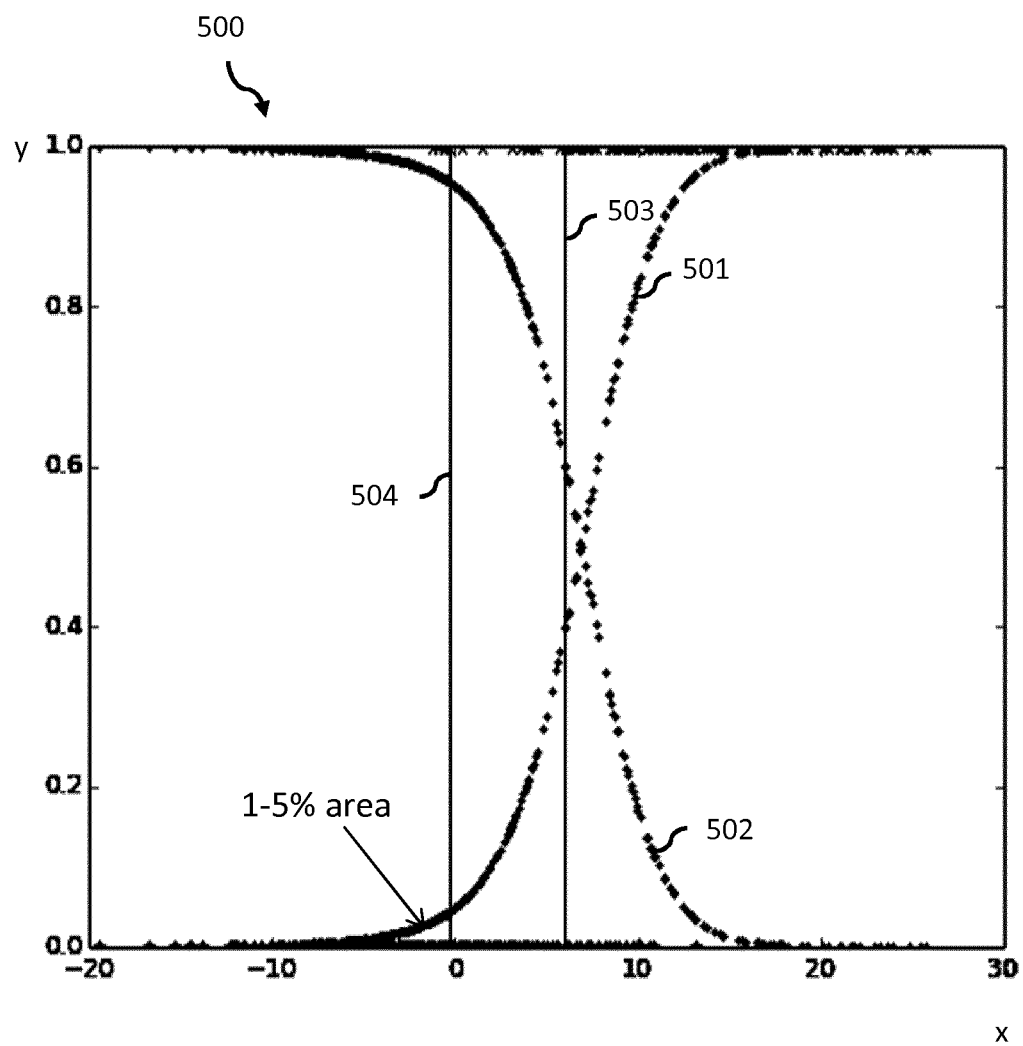
FIG. 5 illustrates an example of a cumulative probability distribution plot of Rust color clusters.

The Bayesian check is based on one or more different predefined thresholds (cf. FIG. 5, thresholds 503, 504). The more restrictive threshold 503 may allow, for example, only 60% of the candidate regions to pass the check, and the less restrictive threshold 504 may allow, for example, between 1% and 5% of discarded positives (corresponding to a candidate region pass rate of 95% to 99%). If no candidate regions are found when using the more restrictive threshold 503, a relaxation can be done using the less restrictive threshold 504. That is, the Bayesian filter 142 is applied iteratively wherein with each iteration a less restrictive threshold value may be selected than in the previous iteration. That is, in case the first iteration of the filter does not result in any candidate region, a second iteration may be performed with the less restrictive threshold. Further iterations may be performed until finally at least one candidate region is identified. This approach further reduces the existence of false positives while ensuring that every candidate region in the image will be segmented for further deeper analysis.

The Bayesian check may be based on statistical color modelling and clustering of an image based on a single color channel (e.g., dark levels of the b channel). However, to handle the increased complexity and variability of new diseases the filter 140 may be advantageously extended for primary segmentation by using a multi-color channel approach. Thereby, as stated before, the filter 140 becomes tunable for new diseases.

The predefined threshold can be determined when training the Bayes classifier over a training dataset. Images in the training dataset are clustered and segmented in the same way as disclosed in the description of the filter 140. Cumulative probability functions (cf. FIG. 5, probability functions 501, 502) of the visual feature values (e.g., color channel, multi-color channel or other visual features) are computed for disease segmented spots (probability function 501) and no-disease segmented spots (probability function 502). The predefined thresholds 503, 504 may be selected by leaving a desired area (e.g., the 1-5% area for the threshold 504) on the cumulative probability function 501 for the spots that represent a particular disease. The more restrictive threshold 503 may be selected to discard a higher percentage of the false positives (e.g., 30%) to further reduce the number of false positives. The training function may be implemented in a dedicated training module of the system 100 or may be implemented as a sub-module of the filter 140.

The Bayesian check may be performed for a plurality of diseases. In this case, the candidate regions depend on the disease which allows subsequent analysis steps to be performed with an increased accuracy. Only suspicious regions (candidate regions) may be used for training and for describing classifiers and descriptors which enables a near real-time determination of diseases as will be shown in more details in the discussion about the disease diagnosis module 150. Training only the segmented candidate for disease/no-disease characterization allows for a better training of the respective discriminative visual features.

For example, the primary segmentation, if performed over selected color channels including Lab, HSL, and specific color channels, can be mapped to properties/visual features of the septoria disease. The segmented region may be refined by means of morphologic operations such as erosions and/or dilations. Image processing can further be tuned to detect the inner and outer regions of septoria-like diseases. Image color statistics taken from one or more selected color channels or a combination of color channels can be calculated and may be used to train a Bayesian segmentation model that is responsible for detecting every blob in the image which is suitable for re-presenting a particular disease. The trained Bayesian model can be biased to avoid discarding true diseased blob candidates by the Bayesian filter 142.

In one embodiment, the filter 140 may not be able to identify 1610 the one or more candidate regions if, for example, the predefined threshold is set in a too restrictive manner (allowing only very few false positives). In such cases the number of hits for candidate regions after the Bayesian check remains zero. In this case, the filter 140 may simply determine 1650 the cluster with the highest probability given by the Bayes Classifier as a candidate region and provide this candidate region to the further detailed analysis steps. In other words, if the Bayesian check with the predefined threshold comes to the decision that there is no candidate region, the restriction regarding the required probability for a candidate region is relaxed and one or more regions with lower probabilities may be selected for further analysis. This ensures that at least the most suitable region which is available on the leaf will be analyzed further.

In one embodiment, the clusterer 141 may be configured to perform a hierarchical clustering over the identified candidate region(s). That is, the clusterer 141 is invoked again after the Bayesian check to further refine the clusters which passed the Bayesian check. This may be advantageous for candidate regions which cover a relatively large area (e.g., >15% of the total leaf area) of the leaf surface when compared to other smaller candidate regions. For example, the comparison check 1660 to decide whether a candidate region is relatively large or not, can be performed on the basis of a dynamically computed threshold where an average value of the size of the initially identified candidate regions and a variance is used to identify such candidate regions which show significant deviations (to the larger) from the average value. The threshold may also depend on the type of disease.

For example, when the filter 140 detects such large candidate regions for certain diseases while performing the identifying 1500 and filtering 1600 steps, the clusterer 141 may repeat the clustering step 1500 just for the large candidate region(s). The filtering 1600 step with the Bayesian check is also repeated, but only for the newly identified sub-clusters resulting from the second execution of the clustering step. This allows the following analysis steps to be more specific regarding the identification of candidate regions. In other words, the larger clusters of the first execution of the clustering step 1500 can be partitioned into further (sub-)clusters during the second execution of the clustering step. The result can be seen as a cluster hierarchy with the larger clusters (candidate regions) identified in the first clustering step 1500 as parent nodes and the partitioning results (sub-clusters) of the second clustering step as child nodes of the respective parent nodes. The re-application of the Bayesian filter 142 to such sub-cluster regions may lead to a better segmentation of the originally large candidate regions and results in more specific smaller candidate regions which can improve the accuracy of the following analysis steps.

Thus, the primary segmentation performed by the filter 140 eliminates such regions in the image that carry useless visual information for the further processing and analysis. This strengthens the following stages of the disease diagnosis process because respective descriptors and classifiers can focus on proper characterization of overlapping visual features rather than characterizing a whole set of different visual characteristics which mostly would have no discriminative power. In other words, the modeling of diseases in terms of their characterizing visual features is focused on such regions of the leaf which can be confused with a diseased region, and not on the entire leaf.

The filter module 140 also can be parametrized to perform specific white balance correction algorithms on the received image data. This can be advantageous when a neutral gray plate is used for capturing images with a mobile device.

In one embodiment, the filter 140 uses a refined mask approach. When performing a normal k-means clustering (cf., https://en.wikipedia.org/wiki/K-means_clustering) observations (smaller regions) are partitioned into bigger clusters in which each observation belongs to the cluster with the nearest mean, serving as a prototype of the cluster. This may lead to a loss of diseased regions that are never analyzed because the respective area is too small in comparison with the total leaf area. This problem may be solved by the refined mask approach. Thereby, the Natural Image Segmentation algorithm which may be used by one embodiment of the leaf extractor 130 is applied to the extracted leaf portions 11e of the image and such regions with no interest (flat regions with no elements) are discarded. This allows to increase the weight of small spots in the primary k-means clustering. (Figures?)

In the following three paragraphs, the filter 140 is disclosed in more details with regards to the plant diseases *Helminthosporium*, Rust and Septoria.

Primary segmentation for *Helminthosporium* disease: the *Helminthosporium* disease is characterized by dark spots on the surface of the leaf. These spots vary in size and sometimes cause de-coloration of the leaf. As a consequence, the primary segmentation is parameterized to detect the dark clusters on the L channel. The Bayes color segmentation classifier 142 is then able to filter out (identify) all real candidate regions while maintaining a low number of false positives.

Primary segmentation for Rust: The Rust disease is characterized by bright yellow spots on the surface of the leaf. In this case, the primary segmentation is parameterized to detect the bright clusters on the mean of the a-b channels. The Bayes color segmentation classifier 142 is then able to filter out (identify) all the real candidate regions while maintaining a low number of false positives.

Primary segmentation for Septoria: Unlike the previously described diseases, the Septoria disease is characterized by a de-coloration spreading over the entire leaf. De-coloration in this context means that the original color of the leaf is disappearing and changes to disease specific color(s). In this case, an opposition color model can be used for detection.

The removal quality of false positives depends on the training of the segmentation model used by the Bayesian classifier. In the training stage, the primary segmentation stage of the filter 140 produces a group of segmented sub-images. Typically, most of these sub-images already belong to the real positives group. However, there are some sub-images that belong to elements which do not belong to a particular group that corresponds to the visual features of a particular disease. Therefore, for training purposes, it may be advantageous to filter these generated sub-images by means of a previously generated segmentation ground truth. In machine learning, the term "ground truth" refers to the annotated data to obtain the accuracy of the training set's classification for supervised learning techniques. This is used in statistical models to prove or disprove research hypotheses. Primary segmentation results can also be analyzed in order to minimize the number of generated false positive sub-images based on previously trained classifiers.

FIG. 5 illustrates, as an example, a distribution plot 500 of Rust color clusters (line 501, top) and no-Rust color clusters (line 502, bottom) and their cumulative probability showing the discriminative power of the Naive-Bayes classifier. Naive-Bayes classifiers are discussed, for example, in "Pattern Recognition and Pattern Recognition and Machine Learning" by Bishop, Springer 2006, page 202, or in the Stanford IR Book, translator Version 2002-2-1 (1.71), section "Text classification and Naive Bayes" available at https://nlp.stanford.edu/IR-book/html/htmledition/contents-1.html. On the x-axis, the value of the color channel is presented, on the y-axis the cumulative probability function is presented. By using a training set of images containing the respective disease (e.g., Rust), a Naïve Bayesian model can be calculated. Looking to the plot 500 of the cumulative probability function of the candidate regions over one selected color channel, the "green" cumulative probability function 501 is calculated. As shown on FIG. 5, the disease presents high values of the color channel. The pre-defined threshold 504 in this example is chosen so that it leaves 95 or 99% of the area on its right. That is, 95-99% of the candidate regions which show visual features associated with the Rust disease (true positives) are identified by the Bayesian filter 142. Only the true positive candidate regions left to the threshold 504 (1-5% area) will be cut off from further analysis. In an embodiment using the more restrictive threshold 503, the more restrictive threshold may be applied first for the Bayesian check. If no candidate regions are found the less restricted threshold 504 may be used in a second iteration of the Bayesian check. There can be more than two predefined thresholds which may be used in further iterations of the Bayesian check. The use of less restrictive threshold(s) 504 reduces the appearance of false positive regions. In the embodiment using the hierarchical clustering, the percentage of 95-99% can be even improved because a further clustering and further filtering steps are performed.

Turning back to FIG. 1, each of the segmented sub-images (candidate regions) passing the filter 140 is then further processed and analyzed by the disease diagnosis module 150. The disease diagnosis module 150 includes a base classifier 151 and a meta-classifier 152 to perform a more detailed analysis on the previously identified candidate region(s).

The base classifier 151 is configured to extract from each candidate region C4, C5, C6, Cn one or more visual features to determine for each candidate region one or more probabilities indicating a particular disease. For this purpose, the base classifier uses a statistical inference method. In one embodiment, the base classifier performs an extraction of descriptors from each candidate region and uses machine learning techniques to determine the one or more probabilities. Examples of such machine learning techniques used by the base classifier include: Support Vector Machine, Random Forest, Ada boost, Neural network, classifier ensembling, Bagging, and decision tree.

In an alternative embodiment, the regions detected by filter 140 are sampled through a random dense approach and a plurality of fixed tiles from these regions are extracted. The size of these tiles is fixed. Examples of possible tile sizes are 128×128 or 256×256. These tiles are provided as input for the base classifier 151. In this embodiment, the base classifier 151 for the characterization of candidate regions performs the extraction of visual features and prediction of probabilities by means of a previously trained deep convolutional neural network architecture to determine the one or more probabilities. In this case, it is the convolutional neural network itself that learns during the training phase which are the relevant features to be extracted for a particular disease, and configures itself to extract those features. These kind of techniques are described in detail in the article Deep learning by Yann LeCun et al. in Nature 521, 436-444 (28 May 2015). In this embodiment, the meta-classifier 152 can perform a max pooling operation over the probabilities extracted from the base classifier.

In any of the two disclosed embodiments of the base classifier 151, the base classifier relies on a training process which requires an extensive training image set. As a preprocessing step, a data augmentation process can be conducted over such training image set, by means of which the original images can be subject to diverse transformations to increase data variability and abundance. Examples of such transformations are: rotations, translations, blurring, affine transformations, or illumination intensity and color modifications.

In the first embodiment, when using machine learning techniques to determine the one or more probabilities, a suitable visual feature description may be needed for accurate disease characterization. The filter 140 extracts the relevant image blobs by providing a robust segmentation of diseased candidate regions based on region and image color statistics. However, the description used for the primary segmentation may not be suitable for an accurate description and characterization of the disease.

In order to properly model the extracted candidate regions, different descriptors may be applied to mathematically describe the subtle differences between the candidate regions that actually present, for example, a particular fungal disease from the other regions where such particular disease is not present. For example, color distribution, visual texture and color-texture descriptors are reasonable candidates for fungal disease description.

Examples of descriptors are:
mean and variance of color coordinate channels where channels can be L, a, b, H, S, L, R, G, B, and specifically designed color channels or opposite color channels;
Histogram descriptor of color coordinate channels where channels can be L, a, b, H, S, L, R, G, B and specifically designed color channels or opposite color channels; and
LBP texture descriptor of color coordinate channels where channels can be L, a, b, H, S, L, R, G, B and specifically designed color channels or opposite color channels.

In literature, opposite color channels are also referred to as opponent color channels (cf. Color Appearance Models, Second Edition, by Mark D. Fairchild, Wiley 2005, pages 17 to 19).

For example, descriptors generated for a particular disease can be extended to support the variability of a plurality of further diseases.

Examples of descriptors which may be used for the identification of Septoria, *Helminthosporium* and Rust diseases are:
Local L,a,b,H,S,R,G or B color channel mean and variance;
Local L,a,b,H,S,R,G or B color channel color histogram;
"Local Opponent Color mapping" histogram;
Local Binary Pattern (LBP) descriptor over L,a,b,H,S,R,G or B channels;
Uniform LBP descriptor over L,a,b,H,S,R,G or B channels;
Uniform LBP descriptor over LOC mapping;
DSIFT like descriptor over L,a,b,H,S,R,G or B channels;
Advanced color filter bank LINC and SLINC; and
any of the previous descriptors that has been quantified and encoded in visual words.

These descriptors can be tuned for the different kinds of fungal diseases by, for example, using a machine learning based training approach that may use the modules disclosed in the context of FIG. 1. A person skilled in the field of machine learning knows how to configure such training methods to identify advantageous descriptors for the discrimination of the different kinds of fungal diseases.

Each candidate region obtained by the filter 140 is now analyzed in order to assess the presence of respective diseases. The above descriptor examples can be configured to analyze different visual features for each candidate region. Each descriptor is associated to a classifier of the base classifier module 151 which is responsible for estimating the disease probability for each candidate region of the image.

Figure 6:
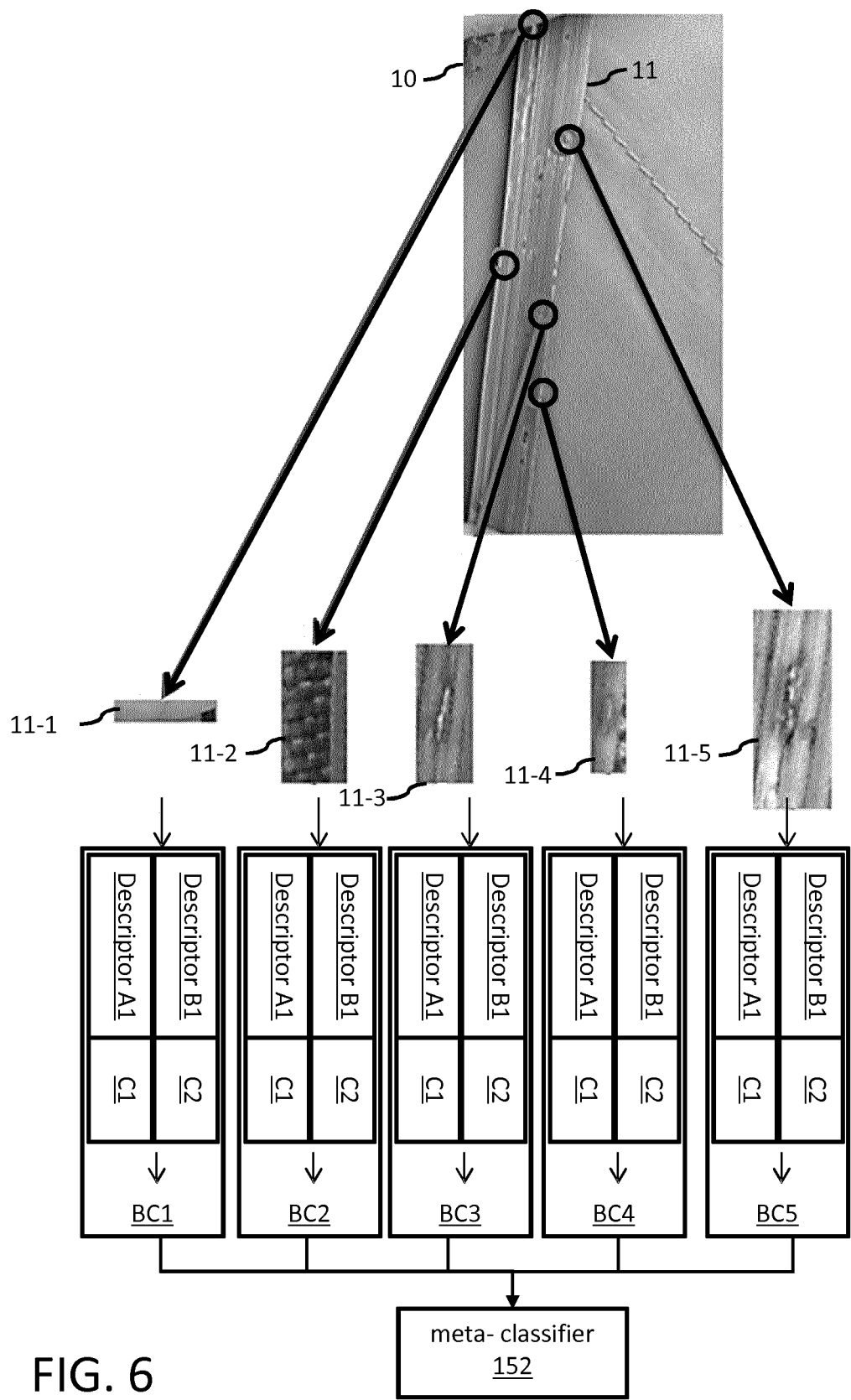
FIG. 6 illustrates details of the diagnosis module according to an embodiment of the invention.

FIG. 6 illustrates such classifiers BC1 to BC5 of the base classifier module. Each detected candidate region 11-1 to 11-5 can be described by means of one or more descriptor-classifier pairs forming the base classifiers. One or more of the above disclosed descriptors may be used to properly describe a particular region. Each descriptor (e.g., Descriptor A1, Descriptor B1) can extract different features, such as for example, color or texture. For example, in one embodiment, the values of the descriptors describe the respective regions by a set of numbers which are fed into a corresponding classifier (e.g., classifiers C1, C2) which returns to its base classifier (e.g., BC5) an estimate for the presence of a particular disease in the respective region according to the corresponding descriptor (e.g., A1).

Each descriptor type may capture different visual features depending on the most discriminative feature in a particular candidate region. For example, descriptor A1 may be of a descriptor type devoted to color features whereas descriptor B1 may be of a descriptor type devoted texture features. In this example, the result would provide two probability estimates for each candidate region. Even when texture and color features are mixed in a unique descriptor, a trained classifier can automatically weight one kind of features over the other features dependent on the dataset distribution. This may cause a less real discriminative power. Therefore, it can be advantageous that each descriptor is associated with a unique classifier that models a particular candidate region in the image.

The classifiers associated to the different descriptors can further be optimized to provide the best discriminative power. Examples of classifiers which may be selected are:
Ada-boost;
Random forest;
SVM;
Bagging classifier; and
Ensemble of classifiers.

The meta-classifier 152 is configured to compute a confidence score CS1 for the particular disease by evaluating all determined probabilities of the candidate regions C4, C5, C6, Cn. Once the different candidate regions have been processed by the base classifier 151, the resulting information is gathered by the meta-classifier 152 which makes a classification decision regarding the entire image for one or more diseases. The information taken into account by the meta-classifier 152 may include:
The probability given by the different descriptors;
The locations of the candidate regions;
The size and shape of the candidate regions;
The weight of each classifier; and
The confidence necessary for an assessment to be taken into account.

Analyzing the results of the proposed algorithm can provide statistics on how the system behaves according to the different confidence levels that can be set. In this way, the system can be set up to a required level of confidence. The higher the required confidence, the more the weighted accuracy of the system will be improved. The system confidence can be estimated by calculating a false acceptance rate FAR and false rejection rate FRR statistics obtained from the training. Given a particular threshold, confidence of the system can be calculated as the FAR if stating that there is a disease present, or it can be calculated as the FRR rate value if stating that there is no disease present.

The previously disclosed segmentation modules, descriptors, classifier and meta-classifier can be integrated sequentially to provide an estimate for the presence of a specific type of disease. Each image to be analyzed is checked by a different Single Disease Classifier object (150) where each classifier verifies the presence of a single disease.

Figure 7A:
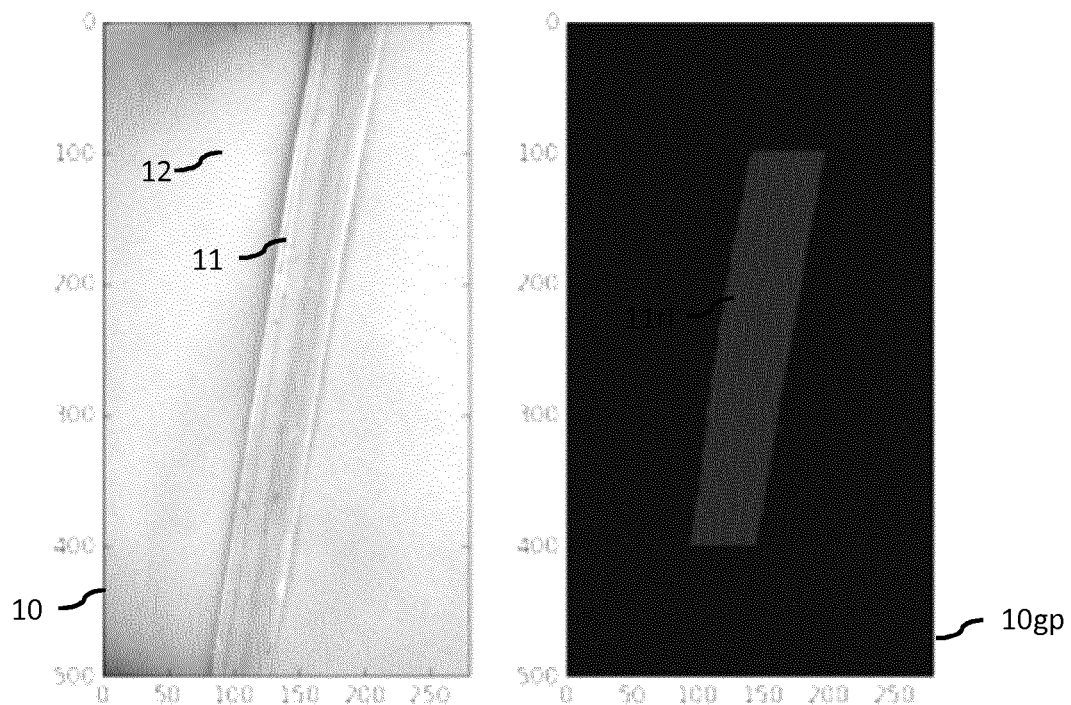
FIGS. 7A to 7C illustrate different possibilities for leaf extraction according to embodiments of the invention.
Figure 7B:
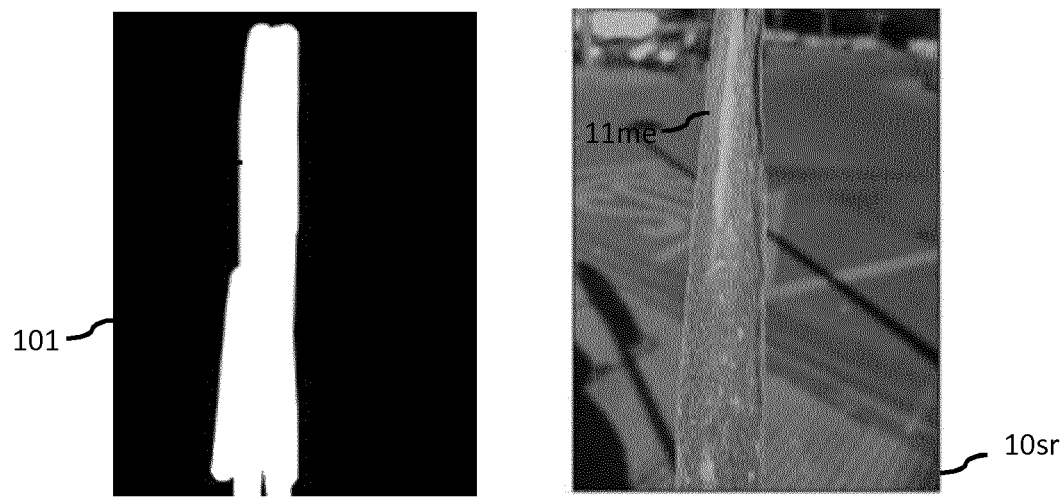
Figure 7C:
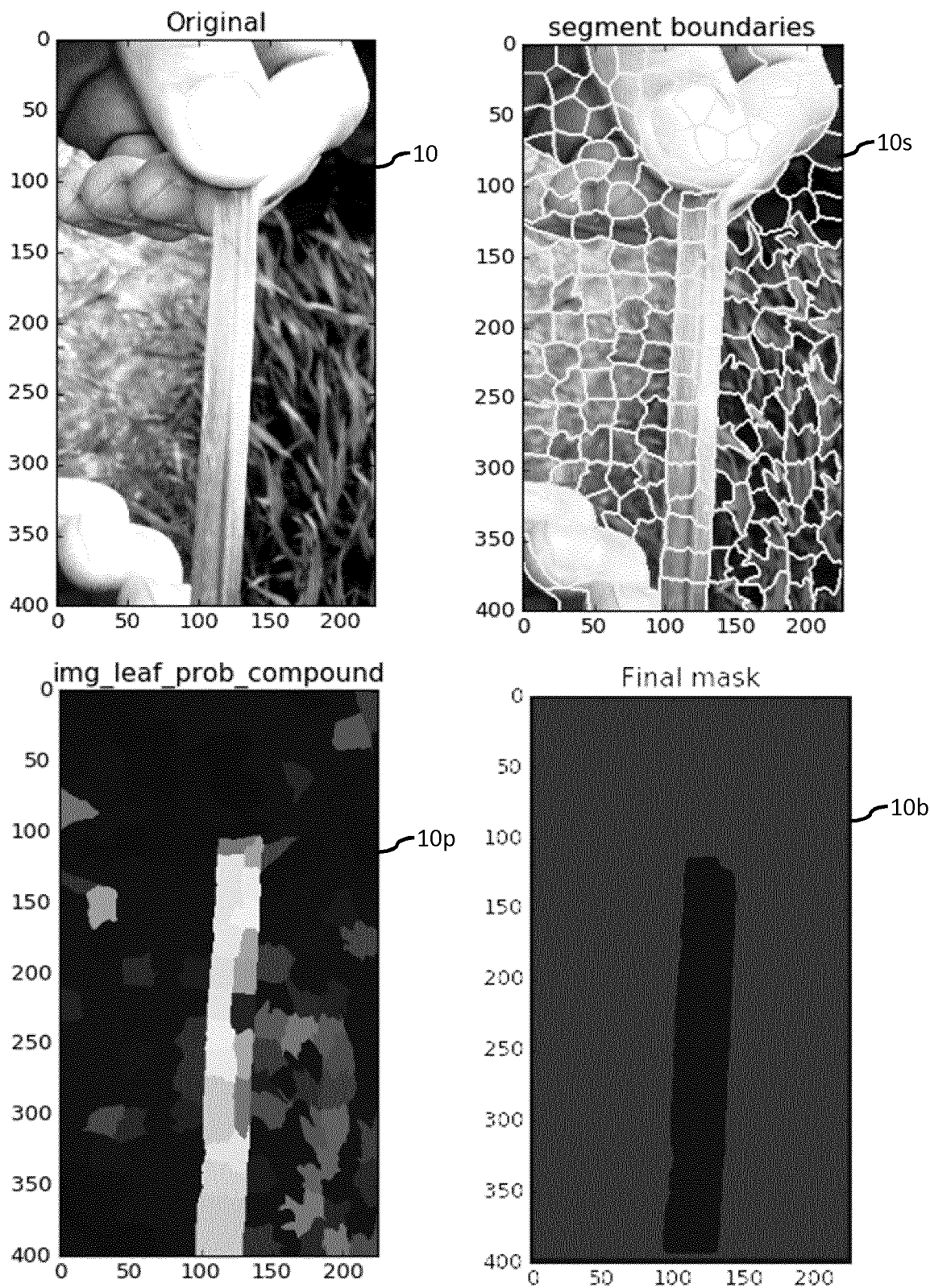

FIGS. 7A to 7C illustrate different possibilities for leaf extraction according to embodiments the invention. FIG. 7A illustrates an embodiment of the leaf extractor based of gray-plate leaf segmentation. In this embodiment, the image 10 (left image in FIG. 7A) is recorded in such a way that the leaf (representation) 11 is placed on a gray plate 12 which provides a normalized background for the entire image 10. The gray-plate leaf segmentation algorithm uses the color saturation and border information in the image 10 and results in the right image 10gp where the region 11ri is segmented as a region of interest corresponding to a portion of the leaf. The gray-plate segmentation algorithm for plant elements assumes that the leaf image is recorded with a gray surface as image background. Other colors may be used as homogenous background color, too. For example, a blue, brown, green, etc. plate may be used with a segmentation algorithm adapted accordingly. The segmentation for the leaf extraction (region 11ri) is performed by means of thresholding and morphology operations.

FIG. 7B illustrates an embodiment of the leaf extractor based of manual leaf segmentation. In this embodiment, the user provides input in the form of a rough estimation of a leaf mask 11um, for example, by drawing the leaf region with a finger or stylus on the recorded image via a touch screen display 101. The mask 11um provided by the user can be further smoothed and refined. For example, Chan-Vese segmentation may be used to smooth and refine the acquired mask. Chan-Vese method may be adapted to get good results over plants. For example, the "a" color channel may be used as segmentation channel and a smoothness μ of 3.0 may be selected. For example, the following term may be used to identify optimal minima corresponding to a region that has a low curvature (first portion of the term) whereas its color characteristics remain constant between the segmented regions:

$$\underset{u,\,C}{\operatorname{argmin}}\;\mu \cdot \operatorname{Length}(C) + \lambda_1 \int_{\Omega_{insideC}} (f(x) - C_1)^2 dx + \lambda_2 \int_{\Omega_{outsideC}} (f(x) - C_2)^2 dx$$

Such smoothing and refining of the user mask 11um avoids selection of leaf borders that could cause misclassification on a disease. The right image 10sr illustrates the result of the manual leaf extraction where the leaf portion lime is finally provided to the subsequent image processing stages.

FIG. 7C illustrates an embodiment of the leaf extractor based of natural image segmentation. In this embodiment, a more complex algorithm is used as the higher variability of the background is more difficult to model. In order to properly segment the leaf, in a first step, the original image 10 is pre-segmented into superpixels or blobs as shown in the segment boundary image 10s with the segment boundaries represented by white lines. Each of these pre-segmented blobs is analyzed in a second step to measure its probability of belonging to a leaf. The result of this second (analysis) step is shown on the image 10p (img_leaf_prob_compound). An example of a superpixel segmentation algorithm than can be used is for this second analysis step is the Simple Linear Iterative Clustering (SLIC) algorithm (cf., R. Achanta, A. Shaji, K. Smith, A. Lucchi, P. Fua, and S. Süsstrunk, "SLIC Superpixels Compared to State-of-the-Art Superpixel Methods," IEEE Transactions on Pattern Analysis and Machine Intelligence, vol. 34, no. 11, pp. 2274-2282, November 2012), which adapts a k-means clustering-based approach in the CIELAB color space while keeping a configurable spatial coherence so as to enforce compactness. Alternative algorithms that can be used for the analysis step with a similar outcome are the Quickshift algorithm (cf., Quick shift and kernel methods for mode seeking, Vedaldi, A. and Soatto, S., European Conference on Computer Vision, 2008) and Felsenszwalb's efficient graph based image segmentation algorithm (cf., Efficient graph-based image segmentation, Felzenszwalb, P. F. and Huttenlocher, D. P. International Journal of Computer Vision, 2004.)

In the second step, various visual features are extracted over each of the segmented superpixels. Each of these features maps each superpixel to a real value, representing a weighting factor or, equivalently, a probability of the superpixel pertaining to the leaf according to such feature. Some examples of the features that can be extracted for each superpixel are:

a) mean, maximum or variance of the magnitude of the edges in the superpixel, based on Roberts' cross operator;
b) mean, maximum or variance of a Gaussian weighting function that depends on the aspect ratio of the image;
c) mean, maximum or variance of the magnitude of the LBP flatness of the superpixel (the rationale behind this is that flatter regions are more likely to be out of focus and thus have no relevance for disease determination);
d) maximum of the average of the b color channel and average of the inverted a color channel; or
e) intra-superpixel perceptual color variance.

In e), the measure of perceptual color variance can be achieved by making use of any of the following CIE-proposed color difference formulae: CIEDE76, CIEDE94, CIEDE2000. In a) to e), the area of the superpixel can optionally be subject to a morphological erosion process in order to minimize the possibility of noise due to inexact segmentations. As a result of the previous process, each superpixel is described by means of one or more of the methods a) to e) with one weight or probability value per method (the kind of features extracted must be the same for all the superpixels, so that they are comparable among them).

In a third step, all the probabilities available for each superpixel are combined together either by means of the product or the sum of the individual probabilities, thus yielding a unique real value in the range [0, 1] for each superpixel, representing its probability of being part of the leaf.

In a forth step, a real threshold value, Th, is selected and the image 10b is binarized so that all the pixels pertaining to a superpixel with combined probability greater or equal such threshold are considered as being part of the leaf. Some examples of threshold selection methods that can be used in this step are: user-given static threshold value, Otsu's threshold selection method (cf., Otsu, N., "A Threshold Selection Method from Gray-Level Histograms," IEEE Transactions on Systems, Man, and Cybernetics, Vol. 9, No. 1, 1979, pp. 62-66.).

As an optional fifth step, a morphological closing method may be utilized in order to get rid of small groups of pixels assigned to the non-leaf class in an isolated manner, thus promoting compactness.

With the same aim, a further optional final step includes keeping only the largest of all the resulting regions of the image labelled as leaf in the previous steps. The resulting set of pixels is labeled as being part of the leaf comprised by the leaf mask.

Figure 8A:
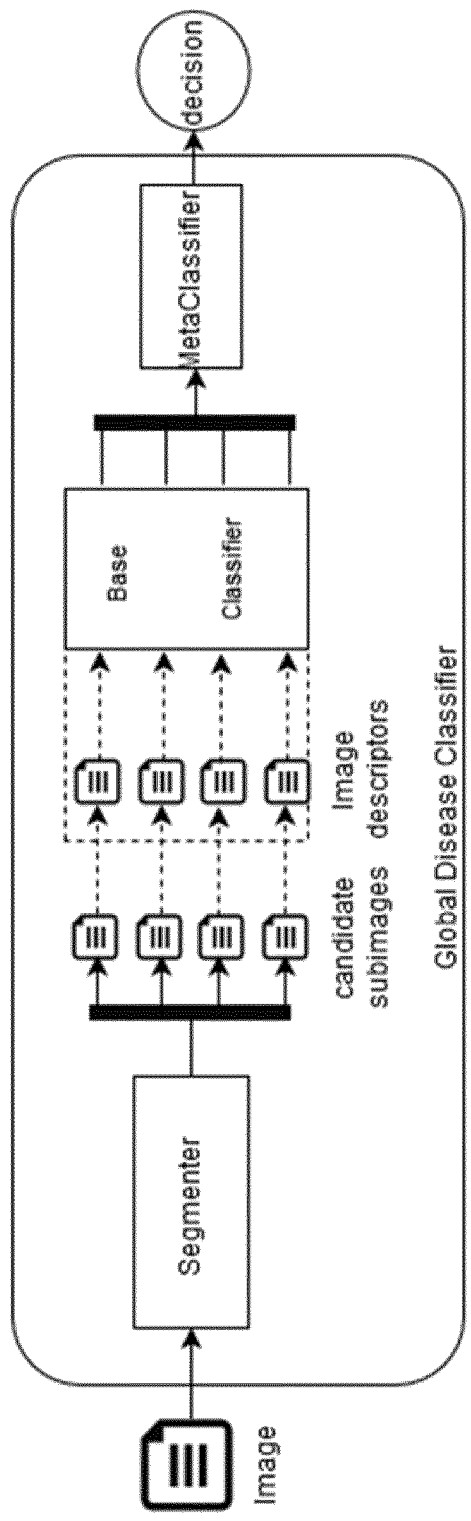
FIGS. 8A, 8B illustrated two embodiments of the systems for single disease and multi disease detection.
Figure 8B:
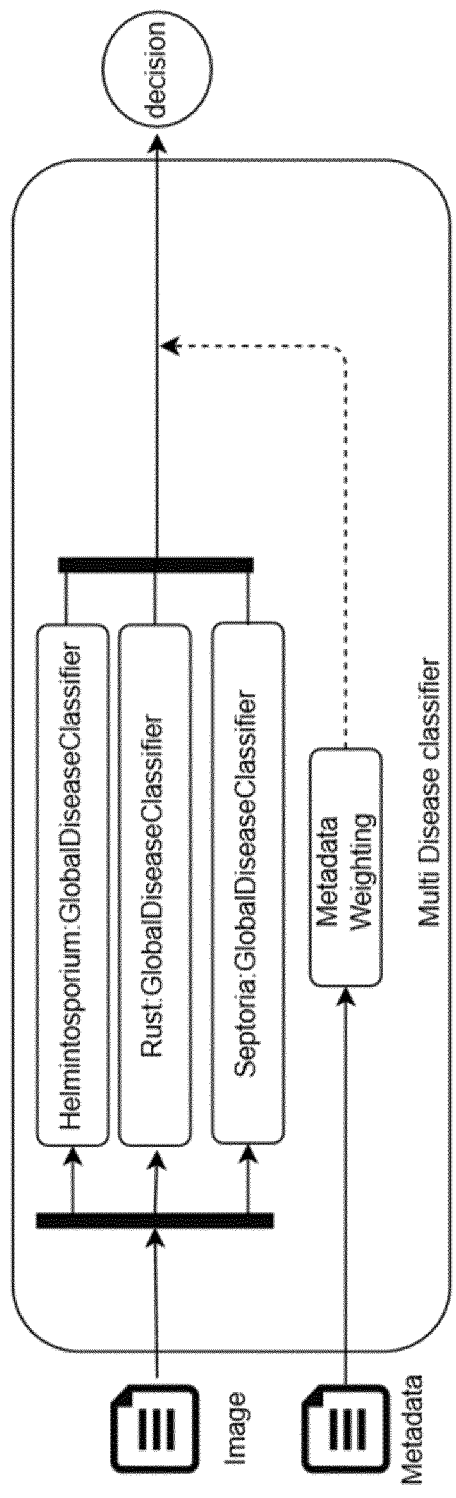

FIGS. 8A, 8B illustrated two embodiments of the systems for single disease and multi disease detection.

FIG. 8A depicts a processing flow for detecting a single disease, where the Image is segmented by a segmenter. The segmenter may include the modules 120, 130 and 140 as disclosed in FIG. 1 to extract the candidate regions (candidate subimages). Each candidate region is thereby described by means of one or more descriptors (image descriptors) and goes into a classifying inference module (e.g., module 150 of FIG. 1), which may include the base classifier submodule. This classifying inference module returns a disease probability for each candidate region. The final decision is weighted by the metaclassifier module.

FIG. 8B illustrates and embodiment where different disease classifiers are put together to classify different diseases (e.g., GlobalDiseaseCalssifiers for *Helminthosporium*, Rust and Septoria) at the same time. A multi-disease classifier may use information from additional metadata (e.g., weather data, date, GPS coordinates, humidity, temperature, previous crop and previous phytosanitary treatments, etc.) and integrate the metadata in the knowledge inference process when summarizing the results from all classifiers. Metadata information can refine the confidence levels given by the Multi Disease classifier. This refinement may be done by a statistical model that can estimate the Bayes probability of the presence of a particular disease in view of the given metadata and the maximum likelihood estimation based on the visual features.

In the following, potential embodiments of the invention are summarized:

Embodiment 1 relates to a system for plant disease detection, comprising: an interface module configured to receive an image of a plant, the image including a visual representation of at least one plant element; a color normalization module configured to apply a color constancy method to the received image to generate a color-normalized image; an extractor module configured to extract one or more image portions from the color-normalized image wherein the extracted image portions relate to the at least one plant element; a filtering module configured: to identify one or more clusters by one or more visual features within the extracted image portions wherein each cluster is associated with a plant element portion showing characteristics of a plant disease; and to filter one or more candidate regions from the identified one or more clusters according to a predefined threshold, by using a naive Bayes classifier, trained on multiple color channels, that models visual feature statistics which are always present on a diseased plant image indicating a particular disease wherein the filtering module is further configured to determine the cluster with the highest probability as candidate region in case no candidate regions are determined when using the predefined threshold; and a plant disease diagnosis module configured: to extract, by using a statistical inference method, from each candidate region one or more visual features to determine for each candidate region one or more probabilities indicating a particular disease; and to compute a confidence score for the particular disease by evaluating all the determined probabilities of the candidate regions to make a classification decision for one or more diseases.

Embodiment 2 relates to the system of embodiment 1, wherein the color normalization module is further configured to apply one or more color constancy methods to the extracted one or more image portions to color-normalize the extracted one or more image portions.

Embodiment 3 relates to the system of embodiments 1 or 2, wherein different plant diseases are associated with different image-disease-characteristics wherein the filtering module is further configured to cluster the extracted image portions by plant disease in accordance with identified image-disease-characteristics.

Embodiment 4 relates to the system of the embodiments 1 to 3, wherein the color constancy method is selected from any one of the group of: Shades of gray algorithm, Gray world algorithm, Gray edge algorithm, and Max-RGB algorithm.

Embodiment 5 relates to the system of the embodiments 1 to 4, wherein the extraction of the one or more image portions from the color normalized image is based on any of the following extraction methods: Gray-plate Segmentation algorithm using color saturation and border information to extract the image portions corresponding to the at least one plant element; Manual Segmentation algorithm receiving a plant element mask as input from a user and using Chan-Vese segmentation to smooth and refine the received mask; and Natural Image Segmentation algorithm using pre-segmentation of the color normalized image by means of color distributions and analyzing each blob with border distribution, color and LBP-based texture to measure its probability of belonging to a plant element.

Embodiment 6 relates to the system of the embodiments 1 to 5, wherein the statistical inference method performs extraction of descriptors and classifiers from each candidate region and uses machine learning techniques to determine the one or more probabilities.

Embodiment 7 relates to the system of the embodiments 1 to 6, wherein the statistical inference method performs visual feature extraction from each candidate region by means of a convolutional neural network architecture and uses deep learning techniques to determine the one or more probabilities.

Embodiment 8 relates to the system of the embodiments 1 to 7, wherein the visual feature statistics is an image color statistics taken from one selected color channel or a combination of color channels selected from the group of: Lab, Mean_ab, RGB, HSI, Norm rgb, CMYK and XYZ.

Embodiment 9 relates to the system of the embodiments 1 to 8, wherein characteristics of a plant disease for clustering are identified using a selected segmentation parameter or a combination or segmentation parameters selected from the following group: number of clusters, the selected recall percentage for the diseased clusters, the color channel, visual textural features, the necessity of a hierarchical clustering or the reduction of the leaf area to cluster based on its visual textural features.

Embodiment 10 relates to the system of the embodiment 6, wherein for feature extraction from the candidate regions a selected descriptor or a combination of descriptors is selected from the group of:—mean and variance of color coordinate channels where channels can be L, a, b, H, S, L, R, G, B, and specifically designed color channels or opposite color channels;—Histogram descriptor of color coordinate channels where channels can be L, a, b, H, S, L, R, G, B and specifically designed color channels such or opposite color channels; and—LBP texture descriptor of color coordinate channels where channels can be L, a, b, H, S, L, R, G, B and specifically designed color channels such or opposite color channels.

Embodiment 11 relates to the system of the embodiment 6 or 10, wherein for feature extraction from the candidate regions a selected classifier or a combination of classifiers is selected from the group of: Support Vector Machine, Random Forest, Ada boost, Neural network, classifier ensembles, and decision tree.

Embodiment 12 relates to the system of the embodiments 1 to 11, wherein one or more visual features for clustering are color descriptors or texture descriptors selected from the group of:—Local L,a,b,H,S,R,G or B color channel mean and variance;—Local L,a,b,H,S,R,G or B color channel color histogram;—"Local Opponent Color mapping" histogram;—Local Binary Pattern (LBP) descriptor over L,a,b, H,S,R,G or B channels;—Uniform LBP descriptor over L,a,b,H,S,R,G or B channels;—Uniform LBP descriptor over LOC mapping;—DSIFT like descriptor over L,a,b,H, S,R,G or B channels;—Advanced color filter bank LINC and SLINC; and any of the previous descriptors quantified and encoded in visual words.

Embodiment 13 relates to the system of the embodiments 1 to 12, wherein the predefined threshold is configured for determining one or more candidate regions and controls the percentage of detected plant element portions to qualify as candidate regions showing characteristics of a plant disease.

Embodiment 14 relates to the system of the embodiments 1 to 13, further comprising: a training module configured to set the predefined threshold by: analyzing a training image dataset using the clustering and filtering function of the filter, and computing cumulative probability functions of visual feature values for spots associated with a disease, and for spots not associated with a disease.

Embodiment 15 relates to a computer-implemented method for detecting plant diseases, comprising: receiving an image of a plant, the image including visual representation of at least one plant element; applying a color constancy method to the received image to generate a color-normalized image; extracting one or more image portions from the color-normalized image wherein the extracted image portions correspond to the at least one plant element; identifying clusters by color channels within the extracted image portions wherein each cluster is associated with a leaf portion showing characteristics of a plant disease; filtering the identified clusters according to a predefined threshold, by using a Bayes classifier that models color statistics which are always present on an image of a diseased plant, the predefined threshold configured for determining one or more candidate regions wherein the predefined threshold defines the percentage of detected plant element portions to qualify as candidate regions showing characteristics of a plant disease wherein filtering is iteratively repeated with at least a further predefined threshold, the further predefined threshold being less restrictive than the predefined threshold, and determining the cluster with the highest probability as candidate region in case no candidate regions are determined when filtering with the predefined threshold; extracting from each candidate region color and texture as complementary features via respective descriptors and classifiers to determine, by using machine learning techniques, for each candidate region one or more probabilities indicating a particular disease; and computing a confidence score for the particular disease by evaluating all determined probabilities of the candidate regions.

Embodiment 16 relates to the method of the embodiment 15, further comprising: prior to identifying, applying a color constancy method to the extracted one or more image portions to color-normalize the extracted one or more image portions.

Embodiment 17 relates to the method of the embodiments 15 to 16, wherein different plant diseases are associated with different image disease characteristics and wherein identifying further comprises: clustering the extracted image portions by plant disease in accordance with the identified image-disease-characteristics.

Embodiment 18 relates to the method of the embodiments 15 to 17, further comprising: determining whether the identified candidate regions include at least one candidate region which exceeds the average size of the identified candidate regions by more than a predefined threshold size, and, if the at least one candidate region is included, repeating the identifying and filtering steps for the at least one candidate region.

Embodiment 19 relates to a computer program product for plant disease detection, comprising instructions that when loaded into a memory of a control system and being executed by at least one processor of the control system cause the control system to perform the method steps according to any one of the embodiments 15 to 18.

Figure 9:
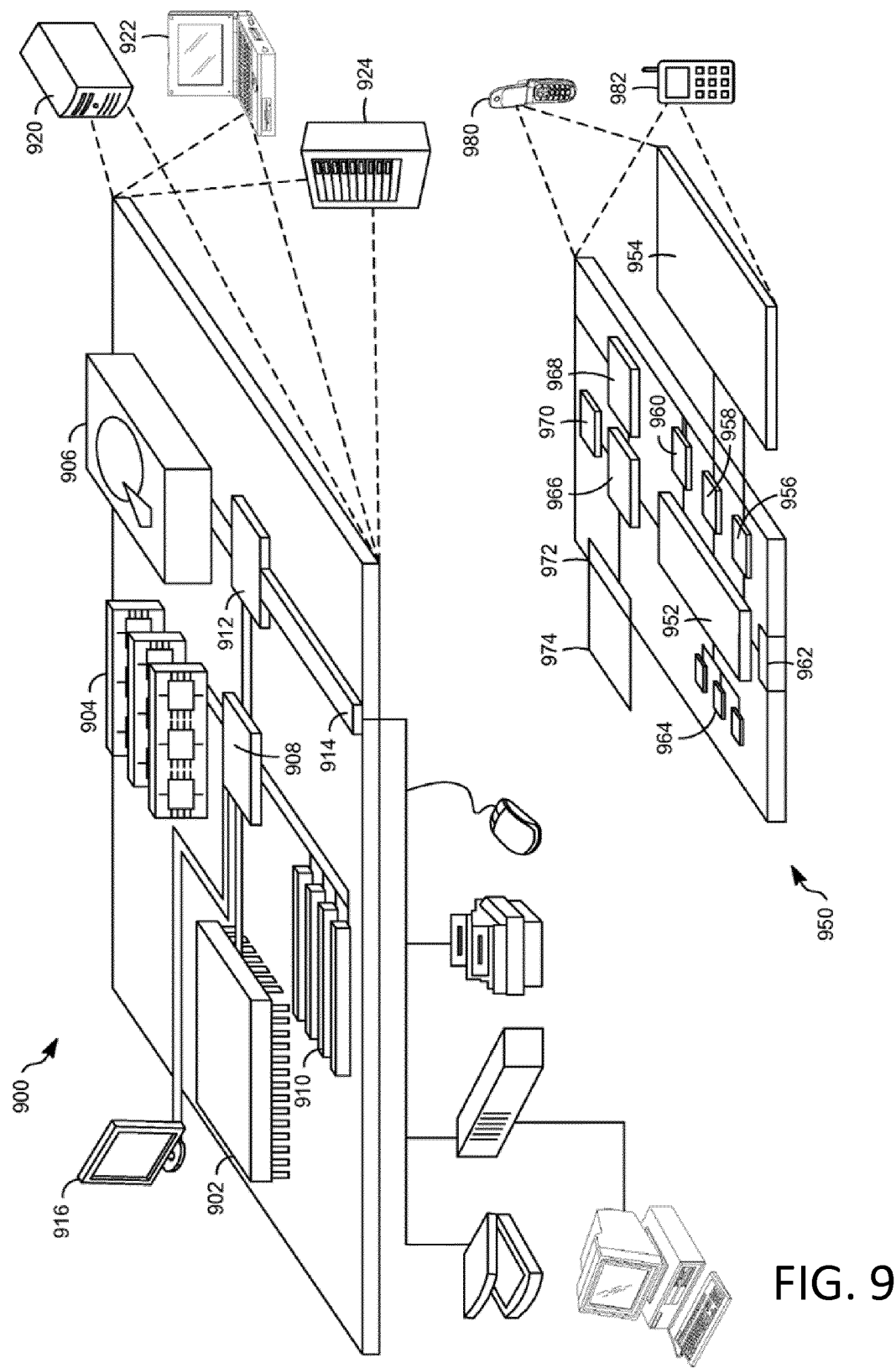
FIG. 9 is a diagram that shows an example of a generic computer device and a generic mobile computer device, which may be used in embodiments of the invention.

FIG. 9 is a diagram that shows an example of a generic computer device 900 and a generic mobile computer device 950, which may be used with the techniques described here. In some embodiments, computing device 900 may relate to the system 100 (cf. FIG. 1). Computing device 950 is intended to represent various forms of mobile devices, such as personal digital assistants, cellular telephones, smart phones, and other similar computing devices. In the context of this disclosure the computing device 950 may provide the camera function to record images which are then provided to the device 900. In other embodiments, the entire system 100 may be implemented on the mobile device 950. The components shown here, their connections and relationships, and their functions, are meant to be exemplary only, and are not meant to limit implementations of the inventions described and/or claimed in this document.

Computing device 900 includes a processor 902, memory 904, a storage device 906, a high-speed interface 908 connecting to memory 904 and high-speed expansion ports 910, and a low speed interface 912 connecting to low speed bus 914 and storage device 906. Each of the components 902, 904, 906, 908, 910, and 912, are interconnected using various busses, and may be mounted on a common motherboard or in other manners as appropriate. The processor 902 can process instructions for execution within the computing device 900, including instructions stored in the memory 904 or on the storage device 906 to display graphical information for a GUI on an external input/output device, such as display 916 coupled to high speed interface 908. In other implementations, multiple processors and/or multiple buses may be used, as appropriate, along with multiple memories and types of memory. Also, multiple computing devices 900 may be connected, with each device providing portions of the necessary operations (e.g., as a server bank, a group of blade servers, or a multi-processor system).

The memory 904 stores information within the computing device 900. In one implementation, the memory 904 is a volatile memory unit or units. In another implementation, the memory 904 is a non-volatile memory unit or units. The memory 904 may also be another form of computer-readable medium, such as a magnetic or optical disk.

The storage device 906 is capable of providing mass storage for the computing device 900. In one implementation, the storage device 906 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 904, the storage device 906, or memory on processor 902.

The high speed controller 908 manages bandwidth-intensive operations for the computing device 900, while the low speed controller 912 manages lower bandwidth-intensive operations. Such allocation of functions is exemplary only. In one implementation, the high-speed controller 908 is coupled to memory 904, display 916 (e.g., through a graphics processor or accelerator), and to high-speed expansion ports 910, which may accept various expansion cards (not shown). In the implementation, low-speed controller 912 is coupled to storage device 906 and low-speed expansion port 914. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 900 may be implemented in a number of different forms, as shown in the figure. For example, it may be implemented as a standard server 920, or multiple times in a group of such servers. It may also be implemented as part of a rack server system 924. In addition, it may be implemented in a personal computer such as a laptop computer 922. Alternatively, components from computing device 900 may be combined with other components in a mobile device (not shown), such as device 950. Each of such devices may contain one or more of computing device 900, 950, and an entire system may be made up of multiple computing devices 900, 950 communicating with each other.

Computing device 950 includes a processor 952, memory 964, an input/output device such as a display 954, a communication interface 966, and a transceiver 968, among other components. The device 950 may also be provided with a storage device, such as a microdrive or other device, to provide additional storage. Each of the components 950, 952, 964, 954, 966, and 968, are interconnected using various buses, and several of the components may be mounted on a common motherboard or in other manners as appropriate.

The processor 952 can execute instructions within the computing device 950, including instructions stored in the memory 964. The processor may be implemented as a chipset of chips that include separate and multiple analog and digital processors. The processor may provide, for example, for coordination of the other components of the device 950, such as control of user interfaces, applications run by device 950, and wireless communication by device 950.

Processor 952 may communicate with a user through control interface 958 and display interface 956 coupled to a display 954. The display 954 may be, for example, a TFT LCD (Thin-Film-Transistor Liquid Crystal Display) or an OLED (Organic Light Emitting Diode) display, or other appropriate display technology. The display interface 956 may comprise appropriate circuitry for driving the display 954 to present graphical and other information to a user. The control interface 958 may receive commands from a user and convert them for submission to the processor 952. In addition, an external interface 962 may be provide in communication with processor 952, so as to enable near area communication of device 950 with other devices. External interface 962 may provide, for example, for wired communication in some implementations, or for wireless communication in other implementations, and multiple interfaces may also be used.

The memory 964 stores information within the computing device 950. The memory 964 can be implemented as one or more of a computer-readable medium or media, a volatile memory unit or units, or a non-volatile memory unit or units. Expansion memory 984 may also be provided and connected to device 950 through expansion interface 982, which may include, for example, a SIMM (Single In Line Memory Module) card interface. Such expansion memory 984 may provide extra storage space for device 950, or may also store applications or other information for device 950. Specifically, expansion memory 984 may include instructions to carry out or supplement the processes described above, and may include secure information also. Thus, for example, expansion memory 984 may act as a security module for device 950, and may be programmed with instructions that permit secure use of device 950. In addition, secure applications may be provided via the SIMM cards, along with additional information, such as placing the identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 964, expansion memory 984, or memory on processor 952, that may be received, for example, over transceiver 968 or external interface 962.

Device 950 may communicate wirelessly through communication interface 966, which may include digital signal processing circuitry where necessary. Communication interface 966 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 968. In addition, short-range communication may occur, such as using a Bluetooth, WiFi, or other such transceiver (not shown). In addition, GPS (Global Positioning System) receiver module 980 may provide additional navigation- and location-related wireless data to device 950, which may be used as appropriate by applications running on device 950.

Device 950 may also communicate audibly using audio codec 960, which may receive spoken information from a user and convert it to usable digital information. Audio codec 960 may likewise generate audible sound for a user, such as through a speaker, e.g., in a handset of device 950. Such sound may include sound from voice telephone calls, may include recorded sound (e.g., voice messages, music files, etc.) and may also include sound generated by applications operating on device 950.

The computing device 950 may be implemented in a number of different forms, as shown in the figure. For example, it may be implemented as a cellular telephone 980. It may also be implemented as part of a smart phone 982, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing device that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing device can include clients and servers. A client and server are generally remote from each other and typically interact through a communication network. The relationship of client and server arises by virtue of computer programs running on the respective computers and having a client-server relationship to each other.

The invention claimed is:

1. A system for plant disease detection, comprising:
an interface module configured to receive an image of a plant, the image including a visual representation of at least one plant element;
a color normalization module configured to apply a color constancy method to the received image to generate a color-normalized image;
an extractor module configured to extract one or more image portions from the color-normalized image wherein the extracted image portions relate to the at least one plant element;
a filtering module configured: to identify one or more clusters by one or more visual features in a plurality of color channels within the extracted image portions wherein each cluster is associated with a plant element portion showing characteristics of a plant disease and different diseases are associated with different color channels; and to filter one or more candidate regions from the identified one or more clusters according to a predefined threshold, by using a naive Bayes classifier being trained by using multi-color channels as features wherein the naive Bayes classifier models visual feature statistics which are always present on a diseased plant image indicating a particular disease, and, in case no candidate region is determined, to iteratively repeat the filtering with at least a further predefined threshold, the further predefined threshold being less restrictive than the predefined threshold, and, in case still no candidate region is determined when using the predefined thresholds, to determine the cluster with a highest probability as a candidate region; and a plant disease diagnosis module configured: to extract, by using a statistical inference method, from each candidate region one or more visual features to determine for each candidate region one or more probabilities indicating a particular disease; and to compute a confidence score for the particular disease by evaluating all the determined probabilities of the candidate regions to make a classification decision for one or more diseases.

2. The system of claim 1, wherein a statistical inference method performs extraction of descriptors and classifiers from each candidate region and uses machine learning techniques to determine the one or more probabilities.

3. The system of claim 1, wherein a statistical inference method performs visual feature extraction from each candidate region by means of a convolutional neural network architecture and uses deep learning techniques to determine the one or more probabilities.

4. The system of claim 1, wherein the visual feature statistics is an image color statistics taken from one selected color channel or a combination of color channels selected from the group of: Lab, Mean_ab, RGB, HSI, Norm rgb, CMYK and XYZ.

5. The system of claim 1, wherein characteristics of a plant disease for clustering by the filtering module are identified using a selected segmentation parameter or a combination of segmentation parameters selected from the groups of visual features including one or more color channels and visual textural features, and configuration features including the number of clusters, the selected recall percentage for the diseased clusters, the necessity of a hierarchical clustering or the reduction of the leaf area to cluster.

6. The system of claim 1, wherein for feature extraction from the candidate regions a descriptor or a combination of descriptors is selected from the group of:

mean and variance of color coordinate channels where channels can be L, a, b, H, S, L, R, G, B, and specifically designed color channels or opposite color channels;

Histogram descriptor of color coordinate channels where channels can be L, a, b, H, S, L, R, G, B and specifically designed color channels such or opposite color channels; and LBP texture descriptor of color coordinate channels where channels can be L, a, b, H, S, L, R, G, B and specifically designed color channels such or opposite color channels.

7. The system of claim 2, wherein for feature extraction from the candidate regions a selected classifier or a combination of classifiers is selected from the groups of: selected classifiers including Support Vector Machine, Adaboost, and Neural network, and classifier ensembles including Random Forest and Bagging.

8. The system of claim 1, wherein one or more visual features for clustering are color descriptors or texture descriptors selected from the group of: Local L,a,b,H,S,R,G or B color channel mean and variance; Local L,a,b,H,S,R,G or B color channel color histogram; Local Opponent Color mapping histogram; Local Binary Pattern (LBP) descriptor over L,a,b,H,S,R,G or B channels; Uniform LBP descriptor over L,a,b,H,S,R,G or B channels; Uniform LBP descriptor over LOC mapping; DSIFT like descriptor over L,a,b,H,S,R,G or B channels; Advanced color filter bank LINC and SLINC; Local L,a,b,H,S,R,G or B color channel mean and variance quantified and encoded in visual words; Local L,a,b,H,S,R,G or B color channel color histogram quantified and encoded in visual words; Local Opponent Color mapping histogram quantified and encoded in visual words; Local Binary Pattern (LBP) descriptor over L,a,b,H,S,R,G or B channels quantified and encoded in visual words; Uniform LBP descriptor over L,a,b,H,S,R,G or B channels quantified and encoded in visual words; Uniform LBP descriptor over LOC mapping quantified and encoded in visual words; DSIFT like descriptor over L,a,b,H,S,R,G or B channels quantified and encoded in visual words; and Advanced color filter bank LINC and SLINC quantified and encoded in visual words.

9. A computer-implemented method for detecting plant diseases, comprising:

receiving an image of a plant, the image including visual representation of at least one plant element;

applying a color constancy method to the received image to generate a color-normalized image;

extracting one or more image portions from the color-normalized image wherein the extracted image portions relate to the at least one plant element;

identifying clusters by color channels within the extracted image portions wherein each cluster is associated with a plant element portion showing characteristics of a plant disease and different diseases are associated with different color channels;

filtering the identified clusters according to a predefined threshold, by using a naive Bayes classifier being trained by using multi-color channels as features wherein the naive Bayes classifier models color statistics which are always present on an image of a diseased plant indicating a particular disease, the predefined threshold configured for determining one or more candidate regions wherein the predefined threshold defines the percentage of detected plant element portions to qualify as candidate regions showing characteristics of a plant disease;

in case no candidate region is determined, iteratively repeating the filtering step with at least a further predefined threshold, the further predefined threshold being less restrictive than the predefined threshold;

in case still no candidate region is determined, determining the cluster with the highest probability as a candidate region;

extracting from each candidate region one or more visual features via respective descriptors and classifiers to determine, by using machine learning techniques, for each candidate region one or more probabilities indicating a particular disease; and computing a confidence score for the particular disease by evaluating all determined probabilities of the candidate regions to make a classification decision for one or more diseases.

10. The method of claim 9, further comprising:
prior to identifying, applying a color constancy method to the extracted one or more image portions to color-normalize the extracted one or more image portions.

11. The method of claim 9, wherein different plant diseases are associated with different image disease characteristics and wherein identifying further comprises:
clustering the extracted image portions by plant disease in accordance with the identified image-disease-characteristics.

12. The method of claim 9, further comprising:
determining whether the identified candidate regions include at least one candidate region which exceeds the average size of the identified candidate regions by more than a predefined threshold size, and, if the at least one candidate region is included, repeating the identifying and filtering steps for the at least one candidate region.

13. A non-transitory computer-readable medium comprising instructions that, when executed by at least one processor, cause the processor to perform the method steps according to claim 9.

* * * * *